(12) United States Patent
Brenner et al.

(10) Patent No.: US 11,592,450 B2
(45) Date of Patent: Feb. 28, 2023

(54) DIAGNOSIS AND RISK STRATIFICATION OF FUNGAL INFECTIONS

(71) Applicants: B.R.A.H.M.S GmbH, Hennigsdorf (DE); UNIVERSITAT HEIDELBERG, Heidelberg (DE)

(72) Inventors: Thorsten Brenner, Morlenbach (DE); Markus Alexander Weigand, Wettenberg (DE); Florian Uhle, Heidelberg (DE); Darius Cameron Wilson, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 363 days.

(21) Appl. No.: 16/636,235

(22) PCT Filed: Aug. 6, 2018

(86) PCT No.: PCT/EP2018/071305
§ 371 (c)(1),
(2) Date: Feb. 3, 2020

(87) PCT Pub. No.: WO2019/025639
PCT Pub. Date: Feb. 7, 2019

(65) Prior Publication Data
US 2020/0371113 A1    Nov. 26, 2020

(30) Foreign Application Priority Data

Aug. 4, 2017   (EP) ..................................... 17185036

(51) Int. Cl.
*G01N 33/68* (2006.01)

(52) U.S. Cl.
CPC ... *G01N 33/6893* (2013.01); *G01N 2333/525* (2013.01); *G01N 2333/5412* (2013.01); *G01N 2333/5428* (2013.01); *G01N 2333/57* (2013.01); *G01N 2800/26* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,320,022 B1 | 11/2001 | Cuttitta et al. |
| 7,915,002 B2 | 3/2011 | Bergmann |
| 7,939,639 B2 | 5/2011 | Cuttitta et al. |
| 8,507,210 B2 | 8/2013 | Bergmann et al. |
| 9,229,013 B2 | 1/2016 | Bergmann et al. |
| 9,541,549 B2 | 1/2017 | Bergmann et al. |
| 2002/0055615 A1 | 5/2002 | Cuttitta et al. |
| 2007/0004630 A1 | 1/2007 | Cuttitta et al. |
| 2010/0021469 A1 | 1/2010 | Cuttitta et al. |
| 2010/0292131 A1 | 11/2010 | Kas et al. |
| 2011/0086831 A1 | 4/2011 | Bergmann et al. |
| 2012/0094314 A1 | 4/2012 | Bahrami et al. |
| 2013/0203612 A1 | 8/2013 | Graf et al. |
| 2013/0302841 A1 | 11/2013 | Struck et al. |
| 2014/0213507 A1* | 7/2014 | Shirakawa ............. A61K 45/00 514/3.1 |
| 2015/0011017 A1 | 1/2015 | Bergmann et al. |
| 2015/0192595 A1* | 7/2015 | Ng .......................... G01N 33/74 436/501 |
| 2017/0010286 A1 | 1/2017 | Bergmann |
| 2017/0370949 A1 | 12/2017 | Struck et al. |
| 2018/0348235 A1 | 12/2018 | Vigué et al. |
| 2019/0178894 A1 | 6/2019 | Ziera et al. |
| 2019/0376985 A1 | 12/2019 | Bergmann et al. |
| 2021/0156850 A1 | 5/2021 | Anderberg et al. |

FOREIGN PATENT DOCUMENTS

| | | |
|---|---|---|
| EP | 1488209 B1 | 12/2005 |
| EP | 2320237 B1 | 8/2016 |
| WO | 9707214 A1 | 2/1997 |
| WO | 0242770 A1 | 5/2002 |
| WO | 04090546 A1 | 10/2004 |
| WO | 08012019 A2 | 1/2008 |
| WO | WO09062948 A1 | 5/2009 |
| WO | 10128071 A1 | 11/2010 |
| WO | 10139475 A1 | 12/2010 |
| WO | 12059477 A1 | 5/2012 |

(Continued)

OTHER PUBLICATIONS

Anadaluz-Ojeda D. et al. : "Superior accuracy of mid-regional proadrenomedullin for mortality prediction in sepsis with varying levels of illness severity", Intensive Care, vol. 7, Feb. 10, 2017, Article No. 15, pp. 1-8.

Angeletti S. et al. : "Diagnostic and prognostic role of procalcitonin (PCT) and MR-pro-Adrenomedullin (MR-proADM) in bacterial infections", APMIS, vol. 123, No. 9, Jun. 8, 2015 (Jun. 8, 2015), pp. 740-748.

Angeletti S. et al: "Procalcitonin and mid-regional pro-adrenomedullin test combination in sepsis diagnosis", Clinical Chemistry and Laboratory Medicine, De Gruyter, DE, vol. 51, No. 5, Apr. 30, 2013 (Apr. 30, 2013), pp. 1059-1067, XP009502330, ISSN: 1434-6621, DOI: 10.1515/CCLM-2012-0595.

Bruno Viaggi et al: "Mid regional pro-adrenomedullin for the prediction of organ failure in infection. Results from a single centre study", PLOS One, vol. 1 3, No. 8, Aug. 13, 2018 (Aug. 13, 2018), (Continued)

*Primary Examiner* — Oluwatosin A Ogunbiyi
(74) *Attorney, Agent, or Firm* — Millen, White, Zelano & Branigan, PC; Ryan Pool

(57) ABSTRACT

The invention relates to a method for the diagnosis and/or risk stratification of invasive fungal infections (IFI)/invasive fungal diseases (IFD) and in particular associated with sepsis or septic shock, wherein a determination of the marker proadrenomedullin (proADM) or a partial peptide or fragment thereof, in particular midregional proadrenomedullin (MR-proADM), or contained in a marker combination (panel, cluster), is carried out from a patient to be examined. Furthermore, the invention relates to a diagnostic assay and a kit for carrying out the method.

18 Claims, 3 Drawing Sheets
Specification includes a Sequence Listing.

(56) References Cited

FOREIGN PATENT DOCUMENTS

| WO | 13086359 A1 | 6/2013 |
|---|---|---|
| WO | 14147153 A1 | 9/2014 |
| WO | 17089474 A1 | 6/2017 |
| WO | 18007588 A1 | 1/2018 |
| WO | 18029214 A1 | 2/2018 |

OTHER PUBLICATIONS p. e0201491, xP055535888, DOI: 1 0137 1/journal.pone.0201 491.
Cairon Pietr—et al: "Circulating Biologically Active Adrenomedullin such statement (bio—ADM) Predicts Hemodynamic support Requirement and Mortality During Sepsis", Chest, vol. 152, No. 2, Aug. 1, 2017 (Aug. 1, 217), pp. 312-320, XP55430860.
Caroline Guignant et al: "Assessment of pro-vasopressin and proadrenomedullin as predictors of 28-day mortality in septic shock patients", Intensive Care Medicine, vol. 35, No. 1 1, Aug. 7, 2009 (Aug. 7, 2009), pp. 1859-1867, xP055535903, DE ISSN: 0342-4642, DOI: 10.1 007is001 34-009-1 610-5.
Charles P.-E. et al.: "MR-ProADM elevation upon ICU admission predicts the outcome of septic patients and is correlated with upcoming fluid overload", Shock, vol. 48, No. 4, Oct. 2017, pp. 418-426.
Christ-Crain M El AL: "Biomarkers in respiratory tract infections: diagnostic guides to antibiotic prescription, prognostic markers and mediators", European Respiratory Journal, Munksgaard International Publishers, Copenhagen, DK, vol. 30, No. 3, Aug. 31, 2007 (Aug. 31, 2007), pp. 556-573, XP00950261 1.
Christ-Crain M.: "Procalcitonin Guidance of Antibiotic in Community-acquired Pneumonia: A Randomized Trial", American Journal of Respiratory Critical Care Med—Cine, vol. 174, No. (Jan. 1, 2006), pp. 84-93, XP055021 728, ISSN: 1 073-449X, DOI: 10.11 64/rccm.200512-1 9220C.
Christ-Crain Mirjam et al: "Mid-regional proadrenomedullin as a prognostic marker in sepsis: an study", Critical Care, Biomed Central London, GB, vol. 9, No. 6, Nov. 15, 2005 (Nov. 15, 2005), pp. R81 6-R824, XP021 012417, ISSN: 1364-8535, DOI: 10.11 86/CC3885.
De Jong Evelien El AL: "Efficacy and safety of procalcitonin guidance in reducing the duration of antibiotic treatment—n critically patients: a randomised, controlled, open-label trial", Lancet Infectious Diseases, Elsevier Lid, US, vol. 16, No. 7,Mar. 2, 2016 (Mar. 2, 2016), pp. 819-827, XP02961 8593.
De La Torre-Prados Maria V et al: "Mid-regional proadrenomedullin as prognostic biomarker in septic shock", Minerva Anestes—Olog—CA G—Ornale Italiano Di Anestesia E D—Analg, Societa Italiana Di An Estesiolog Ia, IT, vol. 82, No. 7, Jul. 1, 2016 (Jul. 1, 2016), pp. 760-766, XP0091 92235,ISSN 1827-1596.
Elke G. et al.: "The use of mid-regional proadrenomedullin to identify disease severity and treatment response to sepsis-a secondary analysis of a large randomised controlled trial", Crit. Care, vol. 22, No. 1, 79, Mar. 21, 2018 (Mar. 21, 2018), pp. 1-12, XP55556348.
Gille Jochen et al: "MR-proADM: A New Biomarker for Early Diagnosis of Sepsis in Burned Patients", Journal of Burn Care & Research, Williams & Wilkins, US, vol. 38, No. 5, Aug. 31, 2017 (Aug. 31, 2017), pp. 290-298, XP009502061.
Hartmann Oliver et al: "Time-dependent Cox regression: Serial measurement of the cardiovascular biomarker proadrenomedullin—mproves survival prediction in patients with—ower resp—ratory infection", International Journal of Cardiology, vol. 161, No. 3, Sep. 24, 2012, p. 166-173, XP028959234.
Michels M et al: "High plasma mid-regional pro-adrenomedullin—evels in children with severe dengue virus—nfections", Journal of Clinical Virology, Elsevier, Amsterdam, NL, vol. 50, No. 1, Jan. 1, 2011 (Jan. 1, 2011), pp. 8-12, XP027588087.
Munirah Al Shuaibi et al: "Pro-adrenomedullin as a Novel Biomarker for Predicting Infections and Response to Antimicrobials in Febrile Patients With Hematologic Malignancies", Cli N Ical I Nfectious Diseases, vol. 56, No. 7,Jan. 3, 2013 (Jan. 3, 2013), pp. 943-950, XP055535801, US ISSN: 1 058-4838, DOI: 10.1 O93icidicis1 029.
Ereira J.M. et al: "Mid-regional proadrenomedullin: An early marker of response in critically community-acquired pneumonia?", Revista Portugu Esa De Pneumologia (English Edition), vol. 22, No. 6, Nov. 1, 2016 (Nov. 1, 2016), pp. 308-314, XP0554451 19, ISSN: 2173-5115, DOI: 10.1016/j.rppnen.2016 .03.012.
Ossella Marino et al: "Plasma adrenomedullin is associated with short-term mortality and vasopressor requirement in patients admitted with sepsis", Critical Care, Biomed Central Ltd., London, GB, vol. 18, No. 1, Feb. 17, 2014 (Feb. 17, 2014), p. R34, XP021179720, ISSN: 1364-8535, DOI: 10.1 186/CC13731.
Saeed K. et al.: "The early identification of disease progression in patients with suspected infection presenting to the emergency department: a multi-centre derivation and validation study", Crit. Care, vol. 23, No. 1, 40, Feb. 8, 2019 (Feb. 8, 2019), pp. 1-15, XP55556343, the whole document.
Schuetz Philipp et al: "Blood biomarkers for personalized treatment and patient management decisions in community-acquired pneumonia", Current Opinion On Infectious Diseases., vol. 26, No. 2, Apr. 1, 2013 (Apr. 1, 2013), pp. 159-167, XP055439092.
Sebastian Decker et al: Immune—Response Patterns and Next Generation Sequencing Diagnostics for the Detection of Mycoses in Patients with Septic Shock-Results of a Combined Clinical and Experimental Investigation, International Journal of Molecular Sciences, vol. 18, No. 8, Aug. 18, 2017 (Aug. 18, 2017), p. 1796, XP055417185, DOI: 10.3390/ijm518081796.
Shuaibi M. Al et al: "Pro-adrenomedullin as a Novel Biomarker for Predicting Infections and Response to Antimicrobials in Febrile patients With Hematologic Malignancies", Clinical Infectious Diseases, vol. 56, No. 7 ,Jan. 3, 2013, p. 943-950, XP055418326.
Siripen Kalayanarooj: "Clinical Manifestations and Management of Dengue/DHF /DSS", Tropical Medicine and Health, vol. 39, No. 4SUPPLEMENT, Jan. 1, 2011 (Jan. 1, 2011), pp. S83-S87, XP055511310.
Thanachartwet Vipa El AL: "Serum Procalcitonin and Peripheral Venous Lactate for Predicting Dengue Shock and/or Organ Failure: A Prospective Observational Study", PLOS Neglected Tropical Diseases, vol. 10, No. 8, Aug. 26, 2016 (Aug. 26, 2016), p. e0004961, XP055511330.
Ueda et al: "Increased plasma levels of adrenomedullin in patients with systemic inflammatory response syndrome ", Amer. J Resp. Crit. Care Med., vol. 160, No. 1, Jul. 1, 1999, pp. 132-136, XP055052609.
Wang R L et al: "Prediction about severity and outcome of sepsis by pro-atrial natriuretic peptide and pro-adrenomedullin", Chin. J. Traumatol, NL, vol. 13, No. 3, Jun. 1, 2010, pp. 152-157, XP027087080.
Bello et al. Prognostic power of proadrenomedullin in community-acquired pneumonia is independent of aetiology. Eur Respir J 2012; 39: 1144-1155.
Cavallazzi et al. Midregional proadrenomedullin for prognosis in community-acquired pneumonia: a systematic review. Respiratory Medicine (2014) 108, 1569e1580.
Courtais et al. Proadrenomedullin, a useful tool for risk stratification in high Pneumonia Severity Index score community acquired pneumonia. American Journal of Emergency Medicine (2013) 31, 215-221.
Curbelo et al. Inflammation biomarkers in blood as mortality predictors in community-acquired pneumonia admitted patients: Importance of comparison with neutrophil count percentage or neutrophil-lymphocyte ratio. PLOS One | https://doi.org/10.1371/journal.pone.0173947 Mar. 16, 2017 (pp. 1-14).
Debiane et al. The utility of proadrenomedullin and procalcitonin in comparison to C-reactive protein as predictors of sepsis and bloodstream infections in critically ill patients with cancer. Crit Care Med. Dec. 2014 (pp. 1-9) DOI: 10.1097/CCM.0000000000000526.
Gordo-Remartinez.Usefulness of midregional proadrenomedullin to predict poor outcome in patients with community acquired pneumonia. PLOS One | DOI:10.1371/journal.pone.0125212 Jun. 1, 2015 (pp. 1-15).

(56) References Cited

OTHER PUBLICATIONS

Hoeboer SH et al. Old and new biomarkers for predicting high and low risk microbial infection in critically ill patients with new onset fever: a case for procalcitonin. Journal of Infection (2012) 64, 484e493.
Huang et al. Midregional proadrenomedullin as a prognostic tool in community-acquired pneumonia. CHEST /136 / 3 / Sep. 2009 pp. 823.
Lundberg et al. Adrenomedullin and endothelin-1 are associated with myocardial injury and death in septic shock patients. Critical Care (2016) 20:178.
Renaud et al. Proadrenomedullin improves Risk of Early Admission to ICU score for predicting early severe community-acquired pneumonia. CHEST /142 / 6 / Dec. 2012 1447.
Schuetz P et al. Circulating precursor levels of endothelin-1 and adrenomedullin, two endothelium-derived, counteracting substances, in sepsis. Endothelium. Endothelium, 14:345-351, 2007.
Suberviola et al. Prognostic value of proadrenomedullin in severe sepsis and septic shock patients with community-acquired pneumonia. Swiss Med Wkly 2012;142:w13542.
Suberviola et al. Hospital mortality prognostication in sepsis using the new biomarkers suPAR and proADM in a single determination on ICU admission. Intensive Care Med 2013, pp. 1-12, DOI 10.1007/s00134-013-3056-z.
Travaglino F et al. Utility of Procalcitonin (PCT) and Mid regional pro-Adrenomedullin (MR-proADM) in risk stratification of critically ill febrile patients in Emergency Department (ED). A comparison with Apache II score. BMC Infect Dis. Aug. 8, 2012 (pp. 1-8).
International Search Report for PCT/EP2018/071305 dated Dec. 5, 2018.
Andaluz-Ojeda, D. et al., "Superior accuracy of mid-regional proadrenomedullin for mortality prediction in sepsis with varying leveles of illness severity," Annals of Intensive Care, 2017, vol. 7, No. 15.
Christ-Crain M. et al., "Mid-regional pro-adrenomedullin as a prognostic marker in sepsis: an observational study," Critical Care, 2005, vol. 9, pp. R816-R824.
De La Torre-Prados, Maria-Victoria et al., "Mid-regional proadrenomedullin as prognostic biomarker in septic shock," Minerva Anestesiologica, Jul. 1, 2016, vol. 82, No. 7, pp. 760-766.
Decker, S. et al., "Immune-Response Patterns and Next Generation Sequencing Diagnostic for the Detection of Mycoses in Patients with Septic Shock-Results of a Combined Clinical and Experimental Investigation," International Journal of Molecular Sciences, Aug. 18, 2017, vol. 18, No. 8.
Cairon Pietr—et al: "Circulating Biologically Active Adrenomedullin such statement (bio -ADM) Predicts Hemodynamic support Requirement and Mortality During Sepsis", Chest, vol. 152, No. 2, Aug. 1, 2017 (Aug. 1, 2017), pp. 312-320, XP55430860.
Pereira J.M. et al: "Mid-regional proadrenomedullin: An early marker of response in critically community-acquired pneumonia?", Revista Portugu Esa De Pneumologia (English Edition), vol. 22, No. 6, Nov. 1, 2016 (Nov. 1, 2016), pp. 308-314, XP0554451 19, ISSN: 2173-5115, DOI: 10.1016/j.rppnen.2016 .03.012.

* cited by examiner

Fig 1

SEQ ID NO 1: amino acid sequence of pre-proADM

```
1     MKLVSVALMY  LGSLAFLGAD  TARLDVASEF  RKKWNKWALS  RGKRELRMSS
51    SYPTGLADVK  AGPAQTLIRP  QDMKGASRSP  EDSSPDAARI  RVKRYRQSMN
101   NFQGLRSFGC  RFGTCTVQKL  AHQIYQFTDK  DKDNVAPRSK  ISPQGYGRRR
151   RRSLPEAGPG  RTLVSSKPQA  HGAPAPPSGS  APHFL
```

```
PAMP          22-41
MR-proADM     45-92
ADM           95-146
CT-proADM     153-185
proADM        22-185
```

DIAGNOSIS AND RISK STRATIFICATION OF FUNGAL INFECTIONS

The invention relates to a method for the diagnosis and/or risk stratification of fungal infections, in particular invasive fungal infections (hereinafter abbreviated as "IFI") and invasive fungal diseases (hereinafter in short referred to as "IFD") associated with sepsis or septic shock, wherein a determination of the marker proadrenomedullin (proADM) or a partial peptide or fragment thereof, in particular midregional proadrenomedullin (MR-proADM), or contained in a marker combination (panel, cluster), is carried out from a patient to be examined. Furthermore, the invention relates to a diagnostic assay and a kit for carrying out the method.

The precursor peptide, which comprises, inter alia, a signal sequence of 21 amino acids at the N-terminus, is referred to as "preproadrenomedullin" (pre-proADM) (Kitamura K, Sakata J, Kangawa K, Kojima M, Matsuo H, Eto T. Cloning and characterization of cDNA encoding a precursor for human adrenomedullin, Biochem Biophys Res Commun 1993: 194:720-725).
Pre-proADM comprises 185 amino acids and has the sequence according to SEQ ID No: 1 (FIG. 1). Known fragments of pre-pro-ADM include PAMP (AA 22-41) (SEQ ID No: 2), MR-pro-ADM (midregional proadrenomedullin) (AA 45-92) (SEQ ID No: 3), ADM (Adrenomedullin) (AA 95-146) (SEQ ID No: 4), CTpro-ADM (Adrenotensin) (AA 153-185) (SEQ ID No: 5) and "proadrenomedullin" (proADM) (AA 22-185) (SEQ ID No: 6).

The well-known peptide adrenomedullin (ADM) is a peptide which comprises 52 amino acids (SEQ ID No: 4) and which comprises the amino acids 95 to 146 of pre-proADM, from which it is formed by proteolytic cleavage. However, it is disadvantageous that because of the lack of stability of the adrenomedullin, as well as its short lifetime in the plasma (Lewis L K, Smith M W, Yandle T G, Richards A M, Nicholls M G. Adrenomedullin measured in human plasma by radioimmunoassay: plasma concentration, adsorption, and storage. Clin Chem. 44:571-7, 1998), no reliable diagnosis can usually take place.

To date, substantially only a few fragments of the peptide fragments formed in the cleavage of the pre-proADM have been more exactly characterized, in particular the physiologically active peptides adrenomedullin (ADM) and "PAMP", a peptide comprising 20 amino acids (22-41) which follows the 21 amino acids of the signal peptide in pre-proADM.

Furthermore, prior art describes how to determine proAdrenomedullin (proADM) and Adrenomedullin in diagnosis (EP0622458B1, Lewis L K, Smith M W, Yandle T G, Richards A M, Nicholls M G. Adrenomedullin (1-52) measured in human plasma by radioimmunoassay: plasma concentration, adsorption, and storage. Clin Chem 1998; 44:571-7; Ueda S, Nishio K, Minamino N, Kubo A, Akai Y, Kangawa K, et al. Increased plasma levels of adrenomedullin in patients with systemic inflammatory response syndrome. Am J Respir Crit Care Med 1999; 160:132-6; Kobayashi K, Kitamura K, Etoh T, Nagatomo Y, Takenaga M, Ishikawa T, et al. Increased plasma adrenomedullin levels in chronic congestive heart failure. Am Heart J 1996; 131:994-8; Kobayashi K, Kitamura K, Hirayama N, Date H, Kashiwagi T, Ikushima I, et al. Increased plasma adrenomedullin in acute myocardial infarction. Am Heart J 1996; 131:676-80), in particular for the purpose of diagnosing sepsis (EP1121600B1).

Moreover, a further fragment of the pro-Adrenomedullin, namely the so-called mid-regional pro-Adrenomedullin (MR-proADM), is disclosed in EP1488209B1 for diagnostic purposes (Struck J, Tao C, Morgenthaler N G, Bergmann A. Identification of an Adrenomedullin precursor fragment in plasma of sepsis patients. Peptides 2004; 25: 1369-72; Morgenthaler N G, Struck J, Alonso C, Bergmann A. Measurement of mid-regional pro-adrenomedullin in plasma with an immunoluminometric assay. Clin Chem 2005; 51:1823-9; Christ-Crain M, Morgenthaler N G, Stolz D, Muller C, Bingisser R, Harbarth S, et al. Pro-adrenomedullin to predict severity and outcome in community-acquired pneumonia [ISRCTN04176397]. Crit Care 2006; 10:R96; Christ-Crain M, Morgenthaler N G, Struck J, Harbarth S, Bergmann A, Muller B. Mid-regional pro-adrenomedullin as a prognostic marker in sepsis: an observational study. Crit Care 2005; 9: R816-24).

N-terminal fragments of (pre)proAdrenomedulin for diagnosis have also been described in EP0622458B1, such as PAMP (Hashida S, Kitamura K, Nagatomo Y, Shibata Y, Imamura T, Yamada K, et al. Development of an ultrasensitive enzyme immunoassay for human pro-adrenomedullin N-terminal peptide and direct measurement of two molecular forms of PAMP in plasma from healthy subjects and patients with cardiovascular disease. Clin Biochem 2004; 37: 14-21).

A C-terminal fragment of (pre)proAdrenomedullin for diagnosis has also been described in EP211155261, namely CT-pro-ADM (Adrenotensin).

Although, the group of fungal infected patients seems to be small, the number of IFI/IFD is growing up due to an increasing number of immunocompromised patients, a more aggressive surgical therapy in older patients with relevant co-morbidities and an increasing number of oncologic diseases (Bassetti M, Righi E, Costa A et al. (2006) Epidemiological trends in nosocomial candidemia in intensive care. BMC Infect Dis 6:21). Within this context three fungal species seem to be most relevant in Europe: *Candida albicans* (*C. albicans*), *Candida glabrata* (*C. glabrata*) and *Aspergillus fumigatus* (Lichtenstern C, Herold C, Mieth M et al. (2015) Relevance of Candida and other mycoses for morbidity and mortality in severe sepsis and septic shock due to peritonitis. Mycoses 58:399-407).

Sepsis-associated mortality in patients suffering from IFI/IFD is known to be high, amounting up to 42% for *Candida* spp. and even much higher for *Aspergillus* spp. (Shorr A F, Gupta V, Sun X et al. (2009) Burden of early-onset candidemia: analysis of culture-positive bloodstream infections from a large U.S. database. Crit Care Med 37:2519-2526; quiz 2535, Trof R J, Beishuizen A, Debets-Ossenkopp Y J et al. (2007) Management of invasive pulmonary aspergillosis in non-neutropenic critically ill patients. Intensive Care Med 33:1694-1703).

Sepsis is generally caused by a dysregulated host response to infection (Singer M, Deutschman C S, Seymour C W et al. (2016) The Third International Consensus Definitions for Sepsis and Septic Shock (Sepsis-3). Jama 315:801-81), is most frequently caused by bacteria, whereas fungal or viral infections are less common (Eggimann P, Garbino J, Pittet D (2003) Epidemiology of *Candida* species infections in critically ill non-immunosuppressed patients. Lancet Infect Dis 3:685-702). Accordingly, fungemia is only present in 3% of unselected sepsis cases (Eggimann (supra)). Contrariwise, fungi are one of the most isolated species recovered from abdominal foci in peritonitis and numerous patients develop fungal colonization during their hospital stay (Eggimann (supra)).

Especially in patients suffering from fungemia, diagnostic weaknesses may contribute substantially to this alarming mortality. Only a small part of affected patients show positive blood-cultures and fungal growth on culture media is known to be very slow. Accordingly, several studies have shown, that IFI/IFD are the most frequently missed diagnoses in critically ill patients (Combes A, Mokhtari M, Couvelard A et al. (2004) Clinical and autopsy diagnoses in the intensive care unit: a prospective study. Arch Intern Med 164:389-392).

What all these amounts to is, that a life-saving antifungal therapy is either missed, or initiated with a minimum delay of 2 to 3 days (Abe M, Kimura M, Araoka H et al. (2016) Is initial serum (1,3)-beta-d-glucan truly associated with mortality in patients with candidaemia? Clin Microbiol Infect 22:576). Such a delay is known to be associated with an increased mortality.

Hereto, there is a need for presenting a reliable diagnosis of IFI/IFD, or for undertaking (risk) stratification, particularly with regard to further clinical decisions and, in particular, with regard to the degree of severity of fungal infections, in particular IFI/IFD associated with sepsis or septic shock.

However, suitability of proadrenomedullin (proADM) or a partial peptide or fragment thereof, in particular midregional proadrenomedullin (MR-proADM) for the diagnosis of IFI/IFD is not disclosed and likewise the diagnosis of IFI/IFD associated with sepsis or septic shock is not disclosed.

SUMMARY OF THE INVENTION

It is the object of the present invention to make available an improved method for the diagnosis and/or risk stratification of fungal infections, in particular IFI/IFD associated with sepsis or septic shock.

This object is accomplished by means of a method for in vitro diagnosis and/or risk stratification of fungal infections, in particular IFI/IFD associated with sepsis or septic shock, wherein a determination of the marker proadrenomedullin (proADM) or a partial peptide or fragment thereof, in particular midregional proadrenomedullin (MR-proADM), or contained in a marker combination (panel, cluster), is carried out from a patient to be examined (referred to hereinafter as method according to the invention). However, midregional proadrenomedullin (MR-proADM) is a preferred embodiment and demonstrates great plasma stability, which is particularly advantageous.

The said fragments according to the invention preferably refer to at least one of the group PAMP (SEQ ID No: 2), MR-pro-ADM (midregional proadrenomedullin) (SEQ ID No: 3), ADM (Adrenomedullin) (SEQ ID No: 4), CT-pro-ADM (Adrenotensin) (SEQ ID No: 5).

Furthermore, the proadrenomedullin (proADM) or a partial peptide or fragment thereof, in particular midregional proadrenomedullin (MR-proADM) according to the invention can demonstrate modifications such as glycolization, lip(o)idization, or derivatization.

In one aspect is provided a method for in vitro diagnosis and/or risk stratification of invasive fungal infections (IFI) and/or invasive fungal diseases (IFD). The method comprises determining (i) the level or amount of, (ii) a change in amount of as compared to a reference sample, or (iii) the presence of, proadrenomedullin (proADM) (SEQ ID No: 6), a partial peptide or fragment thereof, or midregional proadrenomedullin (MR-proADM) (SEQ ID No: 3), from a patient to be examined.

In another aspect is provided a method for in vitro diagnosis and/or risk stratification of invasive fungal infections (IFI) and/or invasive fungal diseases (IFD) associated with sepsis and/or septic shock. The method comprises determining (i) the level or amount of, (ii) a change in amount of as compared to a reference sample, or (iii) the presence of, proadrenomedullin (proADM) (SEQ ID No: 6), a partial peptide or fragment thereof, or midregional proadrenomedullin (MR-proADM) (SEQ ID No: 3), from a patient to be examined.

In another aspect is provided a method of treating invasive fungal infections (IFI) and/or invasive fungal diseases (IFD). The method comprises determining (i) the level or amount of, (ii) a change in amount of as compared to a reference sample, or (iii) the presence of, proadrenomedullin (proADM) (SEQ ID No: 6), a partial peptide or fragment thereof, or midregional proadrenomedullin (MR-proADM) (SEQ ID No: 3), from a patient to be examined. The method also comprises treating the patient if the proADM or MR-proADM is detected, or if the amount of proADM or MR-proADM exceeds the level of a normal healthy patient, or of a patient with a fungal infection or invasive fungal disease. Treatment may comprise administering an antifungal agent to the patient, such as by intravenous administration. In some embodiments, the IFI or the IFD is associated with sepsis or septic shock. In some embodiments, the antifungal agent is selected from the group consisting of polyene antifungal drugs (e.g. (liposomal) amphotericin B), echinocandins (e.g. caspofungin), azole antifungal drugs (e.g. fluconazole), allylamine and morpholine antifungal drugs, and antimetabolite antifungal drugs (e.g. 5-fluorocytosine).

In some embodiments of the above aspects, the fragment thereof is selected from the group consisting of PAMP (SEQ ID No: 2), MR-proADM (midregional proadrenomedullin) (SEQ ID No: 3), ADM (Adrenomedullin) (SEQ ID No: 4), and CT-pro-ADM (Adrenotensin) (SEQ ID No: 5).

In some embodiments of the above aspects, the invasive fungal infections (IFI) or invasive fungal diseases (IFD) are caused by *Candida* spp., *C. albicans*, *C. glabrata*, *Aspergillus* spp. *Aspergillus fumigatus*.

In some embodiments of the above aspects, a determination is additionally carried out with at least one further marker and/or clinical score and/or clinical parameter selected from the group consisting of C-reactive protein (CRP), cytokines, such as TNF-alpha, for example, interleukins (such as IL-10, IL-6, IL-22, IL17A and IL-17B, interleukin-1 ß), procalcitonin and fragments thereof, pro-atrial natriuretic peptide and fragments thereof (such as ANP and pro ANP), pro-arginin vasopressin and fragments thereof (such as AVP, pro-AVP, and copeptin), angiotensin II, endothelin-1, glucans, interferon gamma (INF-gamma), beta-D-glucan, galactomannan, and adhesion molecules, such as VCAM or ICAM, sequential organ failure assessment score (SOFA), simplified acute physiology score (SAPSII score), the Acute Physiology and Chronic Health Evaluation II (APACHE II) score, the Pneumonia Severity Index (PSI) score, age, gender, family history, ethnicity, body weight, body mass index (BMI), systolic blood pressure, diastolic blood pressure, heart rate, temperature from a patient to be examined.

In some embodiments of the above aspects, a parallel determination or a simultaneous determination of the markers is carried out.

In some embodiments of the above aspects, the determinations are carried out on at least one patient sample.

In some embodiments of the above aspects, the determinations are carried out using an automated analysis device or diagnostic assay.

In some embodiments of the above aspects, the determinations are carried out by means of a rapid test, particularly with single-parameter or multi-parameter determinations.

In some embodiments of the above aspects, the stratification of patients is directed to clinical decisions, particularly further treatment by means of medications for the treatment or therapy of invasive fungal infections (IFI) and/or invasive fungal diseases (IFD), particularly invasive fungal infections (IFI) and/or invasive fungal diseases (IFD) associated with sepsis and/or septic shock. In some embodiments, the patients are selected from the group consisting of critically ill patients, in particular those immunomodulated due to medicaments or disease or due to means of inducing, enhancing, or suppressing an immune response including immunocompromised patients and/or severe neutropenia, cancer patients.

In some embodiments of the above aspects, the diagnosis and/or risk stratification takes place for one or more of (i) prognosis, (ii) prophylaxis, (iii) early detection and detection by means of differential diagnosis, (iv) assessment of the degree of severity, and (v) assessing the course of invasive fungal infections (IFI) and/or invasive fungal diseases (IFD), particularly invasive fungal infections (IFI) and/or invasive fungal diseases (IFD) associated with sepsis and/or septic shock, as an accompaniment to therapy.

In some embodiments of the above aspects, after occurrence of the symptoms (t=0), a cut-off (threshold value) of equal or higher than 6.99 nmol/L, after one day (t=1d) a cut-off (threshold value) of equal or higher than 8.53 nmol/L, after two days (t=2d) a cut-off (threshold value) of equal or higher than 5.10 nmol/L of proadrenomedullin (proADM) or a partial peptide or fragment thereof, in particular midregional proadrenomedullin (MR-proADM), is/are significant (specific) and indicative for the said diagnosis and/or risk stratification.

In some embodiments of the above aspects, after occurrence of the symptoms (t=0), after one day (t=1d), after two days (t=2d) a level of less than 5 nmol/L of proadrenomedullin (proADM) or a partial peptide or fragment thereof, in particular midregional proadrenomedullin (MR-proADM) indicates that the patient does not suffer from invasive fungal infections (IFI) and/or invasive fungal diseases (IFD).

In some embodiments of the above aspects, after occurrence of the symptoms (t=0) a level of less than 2 nmol/L of proadrenomedullin (proADM) or a partial peptide or fragment thereof, in particular midregional proadrenomedullin (MR-proADM) indicates that the patient does not suffer from invasive fungal infections (IFI) and/or invasive fungal diseases (IFD).

In another aspect is provided a kit or a diagnostic assay for in vitro diagnosis and/or risk stratification of invasive fungal infections (IFI) and/or invasive fungal diseases (IFD), particularly invasive fungal infections (IFI) and/or invasive fungal diseases (IFD) associated with sepsis and/or septic shock. The kit contains detection reagents for determining the proadrenomedullin (proADM) (SEQ ID No: 6) or a partial peptide or fragment thereof, in particular midregional proadrenomedullin (MR-proADM) (SEQ ID No: 3) thereof, or contained in a marker combination and/or clinical score and/or clinical parameter according to claim 5, and ancillary substances.

BRIEF DESCRIPTION OF THE DRAWINGS

FIG. 1 shows the sequence of preproADM (SEQ ID No. 1) with the related partial sequences and fragments.

In FIG. 2A, plasma concentrations of IL-17A were measured in patients suffering from septic shock with a fungal infection (grey squared box), a fungal colonization (grey plane box) or without any fungal findings (white box). Plasma samples were collected at the onset of septic shock (T0), and 1 day (T1), 2 days (T2), 7 days (T3), 14 days (T4), 21 days (T5) and 28 days (T6) afterwards. Data in box plots are given as median, $25^{th}$ percentile, $75^{th}$ percentile with the $10^{th}$ as well as $90^{th}$ percentile at the end of the whiskers. Concerning symbolism and higher orders of significance: $p<0.05$: *, $p<0.01$: , $p<0.001$: *.

FIG. 2B shows a receiver operating characteristic (ROC) analysis with interleukin (IL)-17A in all participating patients at sepsis onset (T0), and 1 day (T1), 2 days (T2) as well as 7 days (T3) afterwards with regard to the prediction of a fungal infection up to day 28.

In FIG. 3A, plasma concentrations of MR-proADM were measured in patients suffering from septic shock with a fungal infection (grey squared box), a fungal colonization (grey plane box) or without any fungal findings (white box). Plasma samples were collected at the onset of septic shock (T0), and 1 day (T1), 2 days (T2), 7 days (T3), 14 days (T4), 21 days (T5) and 28 days (T6) afterwards. Data in box plots are given as median, $25^{th}$ percentile, $75^{th}$ percentile with the $10^{th}$ as well as $90^{th}$ percentile at the end of the whiskers. Concerning symbolism and higher orders of significance: $p<0.05$: *, $p<0.01$: , $p<0.001$: *.

FIG. 3B shows a receiver operating characteristic (ROC) analysis with midregional proAdrenomedullin (MR-proADM) in all participating patients at sepsis onset (T0), and 1 day (T1), 2 days (T2) as well as 7 days (T3) afterwards with regard to the prediction of a fungal infection up to day 28.

DETAILED DESCRIPTION OF THE INVENTION

Figure 2A:
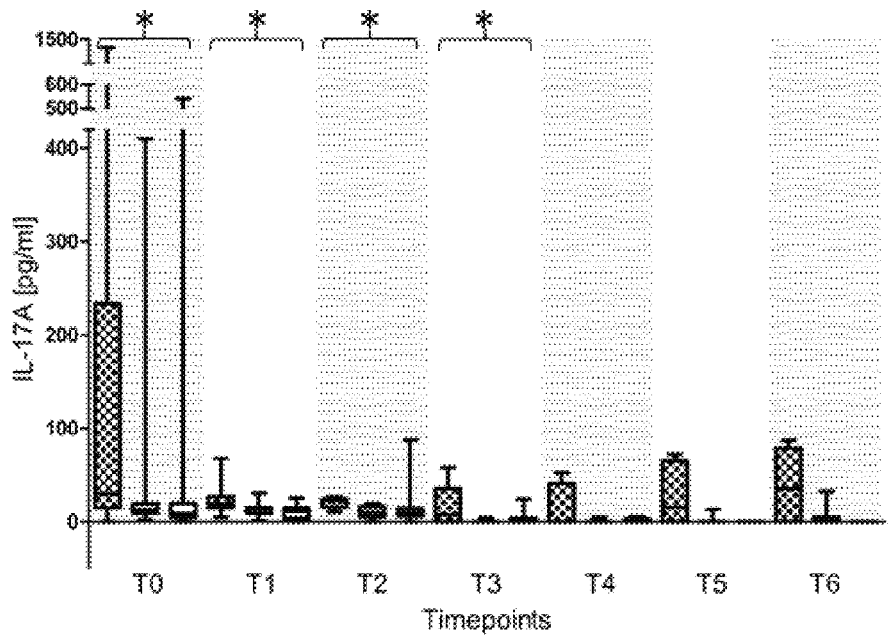
FIGS. 2A and 2B show plasma concentrations of interleukin (IL)-17A in patients with septic shock.

Unless defined otherwise, technical and scientific terms used herein have the same meaning as commonly understood by one of ordinary skill in the art to which this invention belongs.

"Diagnosing" according to the present invention includes determining, monitoring, confirmation, subclassification and prediction of the relevant disease, disorder, complication, or risk. "Determining" relates to becoming aware of a disease, disorder, complication or risk. "Monitoring" relates to keeping track of an already diagnosed disease, disorder, complication or risk, e.g. to analyze the progression of the disease or the influence of a particular treatment on the progression of disease or disorder. "Confirmation" relates to the strengthening or substantiating a diagnosis already performed using other indicators or markers. "Subclassification" relates to further defining a diagnosis according to different subclasses of the diagnosed disease, disorder, complication or risk, e.g. defining according to mild and severe forms of the disease. "Prediction" relates to prognosing a disease disorder or complication before other symptoms or markers have become evident or have become significantly altered.

The term "diagnosis," according to the invention, can comprise finding patients having IFI/IFD, in particular IFI/IFD associated with sepsis or septic shock, with the worse prognosis, for the purpose of intensive diagnosis and therapy/treatment of IFI/IFD, with the goal of allowing as advantageous a course of the IFI/IFD as possible.

In the present invention, the term "risk stratification" relates to the grouping of subjects into different risk groups according to their further prognosis. Risk stratification also relates to stratification for applying preventive and/or therapeutic measures.

For this reason, it is particularly advantageous that a reliable diagnosis and/or risk stratification can take place by means of the method according to the invention. The method according to the invention allows clinical decisions that lead to a more rapid diagnosis of fungal infections in critically ill patients. The method according to the invention allows clinical decisions that lead to a more rapid diagnosis of the IFI/IFD, in particular IFI/IFD associated with sepsis or septic shock. Such clinical decisions also comprise further treatment using medications, for the treatment or therapy of the IFI/IFD, in particular IFI/IFD associated with sepsis or septic shock.

Appropriate treatment requires early diagnosis and differentiation of IFI/IFD, in particular IFI/IFD associated with sepsis or septic shock, even upon emergency room admission, in conjunction with clinical decisions. Since clinical symptoms in IFI/IFD are unspecific and recent diagnostic tools for the detection of fungal pathogens are associated with relevant weaknesses, the differentiation and delineation from other infectious diseases caused by, e.g., bacterial or viral pathogens, as well as the identification of IFI/IFD, in particular IFI/IFD associated with sepsis or septic shock are essential.

Such clinical decisions also comprise further therapy by means of medications for treatment or therapy of IFI/IFD, in particular IFI/IFD associated with sepsis or septic shock, wherein at least one antifungal agent is used, like polyene antifungal drugs (e.g. (liposomal) amphotericin B), echinocandins (e.g. caspofungin), azole antifungal drugs (e.g. fluconazole), allylamine and morpholine antifungal drugs, antimetabolite antifungal drugs (e.g. 5-fluorocytosine).

In another preferred embodiment of the method according to the invention, diagnosis and/or risk stratification take place for assessing the course of fungal infections, in particular IFI/IFD associated with sepsis or septic shock.

In another preferred embodiment of the method according to the invention, diagnosis and/or risk stratification take place for the course of IFI/IFD as an accompaniment to therapy and to adjust therapeutic treatment such as for example mechanical ventilation, renal replacement therapy or antifungal therapy.

The adjustment of a therapeutic treatment may also include the decision whether the subject is treated further as done before or whether the treatment is adapted. For example, the adjustment of the therapeutic treatment may be whether the subject is kept on the intensive care unit (ICU) or emergency department (ED) or whether it is released.

In another preferred embodiment of the method according to the invention, the early detection or early diagnosis of IFI/IFD in accordance with the embodiments of the invention is conducted after occurrence of the symptoms (t=0), or within or after one day (t=1d), or within or after two days (t=2d).

In another preferred embodiment, the invention relates a method for diagnosis and/or risk stratification of IFI/IFD, in particular IFI/IFD associated with sepsis or septic shock, or to a method for in vitro diagnosis for early or differential diagnosis or prognosis of IFI/IFD, in particular IFI/IFD associated with sepsis or septic shock, according to one of the above embodiments, where after occurrence of the symptoms (t=0), a cut-off (threshold value) of equal or higher than 6.99 nmol/L, after one day (t=1d) a cut-off (threshold value) of equal or higher than 8.53 nmol/L, after two days (t=2d) a cut-off (threshold value) of equal or higher than 5.10 nmol/L of proadrenomedullin (proADM) or a partial peptide or fragment thereof, in particular midregional proadrenomedullin (MR-proADM), is/are significant (specific) and indicative for the said diagnosis and/or risk stratification (cf. FIG. 3).

In another preferred embodiment, the invention relates a method for diagnosis and/or risk stratification of IFI/IFD, in particular IFI/IFD associated with sepsis or septic shock, or to a method for in vitro diagnosis for early or differential diagnosis or prognosis of IFI/IFD, in particular IFI/IFD associated with sepsis or septic shock, according to one of the above embodiments, where after occurrence of the symptoms (t=0), after one day (t=1d), after two days (t=2d), a level of less than 5 nmol/L of proadrenomedullin (proADM) or a partial peptide or fragment thereof, in particular midregional proadrenomedullin (MR-proADM) indicates that the patient does not suffer from IFI/IFD. Hence, a patient is to rule-out of IFI/IFD by such a rule-out diagnosis (cf. FIG. 3).

In another preferred embodiment, the invention relates a method for diagnosis and/or risk stratification of IFI/IFD, in particular IFI/IFD associated with sepsis or septic shock, or to a method for in vitro diagnosis for early or differential diagnosis or prognosis of IFI/IFD, in particular IFI/IFD associated with sepsis or septic shock, according to one of the above embodiments, where after occurrence of the symptoms (t=0) a level of less than 2 nmol/L of proadrenomedullin (proADM) or a partial peptide or fragment thereof, in particular midregional proadrenomedullin (MR-proADM) indicates that the patient does not suffer from IFI/IFD. Hence, a patient is to rule-out of IFI/IFD by such a rule-out diagnosis (cf. FIG. 3).

"Sepsis" in the context of the invention refers to a systemic response to infection. Alternatively, sepsis may be seen as the combination of SIRS with a confirmed infectious process or an infection. Sepsis may be characterized as clinical syndrome defined by the presence of both infection and a systemic inflammatory response (Levy M M et al. 2001 SCCM/ESICM/ACCP/ATS/SIS International Sepsis Definitions Conference. Crit Care Med. 2003 April; 31(4): 1250-6). The term "sepsis" used herein includes, but is not limited to, sepsis, severe sepsis, and septic shock. Severe sepsis in this context means sepsis associated with organ dysfunction, hypoperfusion abnormality, or sepsis-induced hypotension. Hypoperfusion abnormalities include lactic acidosis, oliguria and acute alteration of mental status. Sepsis-induced hypotension is defined by the presence of a systolic blood pressure of less than about 90 mm Hg or its reduction by about 40 mm Hg or more from baseline in the absence of other causes for hypotension (e.g. cardiogenic shock). Septic shock is defined as severe sepsis with sepsis-induced hypotension persisting despite adequate fluid resuscitation, along with the presence of hypoperfusion abnormalities or organ dysfunction (Bone R C., Balk R A., Cerra F B., Dellinger, R P., Fein A M., Knaus W A., Schein R M., Sibbald W J., Definitions for sepsis and organ failure and guidelines for the use of innovative therapies in sepsis. The ACCP/SCCM Consensus Conference Committee. American College of Chest Physicians/Society of Critical Care Medicine. Chest 1992, 101(6), 1644-55).

The term "sepsis" also includes severe sepsis or septic shock based on the SEPSIS-2 definition (Bone et al., 2009).

The term "sepsis" also includes subjects falling within the SEPSIS-3 definition (Singer M., Deutschmann C S, Seymour C W, Shankar-Hari M, Annane D, Bauer M., Bellomo R., Bernard G R, Chiche J D, Coopersmith C M, Hotchkiss R S, Levy M M, Marshall J C, Martin G S, Opal S M, Rubenfeld, van der Poll T, Vincent J L, Angus D C. The Third International Consensus Definitions for Sepsis and Septic Shock (Sepsis-3). JAMA 2016, 315 (8), 801-810).

The term "sepsis" used herein relates to all possible stages in the development of sepsis.

As used herein, "infection" within the scope of the invention means a pathological process caused by the invasion of normally sterile tissue or fluid by potentially pathogenic agents/pathogens, organisms and/or microorganisms, and relates preferably to infection(s) by fungi, bacteria, viruses, and/or parasites. Accordingly, the infection can be a bacterial infection, viral infection, and/or fungal infection. The infection can be a local or systemic infection. Further, the subject suffering from an infection can suffer from more than one source(s) of infection simultaneously. For example, the subject can suffer from a viral infection and fungal infection; from a bacterial and fungal infection, and from a bacterial infection, fungal infection and viral infection.

Particularly, the subject suffers from sepsis, severe sepsis or septic shock. Further, the subject may suffer from a respiratory disease, preferably an infection of the lower respiratory tract. As used herein respiratory disease comprises pathological conditions affecting the organs and tissues that make gas exchange possible in higher organisms, and also includes conditions of the upper respiratory tract, trachea, bronchi, bronchioles, alveoli, pleura and pleural cavity, and the nerves and muscles of breathing.

Further, the subject may suffer from an abdominal disease, preferably an infection of the abdominal area comprising the gastrointestinal tract (stomach, large intestine, small intestine), liver, spleen and pancreas.

In another preferred embodiment of the method according to the invention, samples of bodily fluids, particularly blood, serum, plasma, cerebrospinal fluid, urine, saliva, sputum, and pleural effusions, preferably whole blood, serum, or plasma or a mixture thereof, are taken from the patient to be examined, and the diagnosis takes place in vitro/ex vivo, i.e. outside of the human or animal body. In addition, one of skill in the art would realize that some test samples would be more readily analyzed following a fractionation or purification procedure, for example, separation of whole blood into serum or plasma components.

Thus, in a preferred embodiment of the invention the sample is selected from the group consisting of a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The diagnosis and/or risk stratification can take place on the basis of the determination of the mature adrenomedullin or proadrenomedullin (proADM) or a partial peptide or fragment thereof, in particular midregional proadrenomedullin (MR-proADM), and its amount or level that is present, or a change in amount or level, as compared with a reference, in at least one patient sample.

The term "level" or "amount" in the context of the present invention relates to the concentration (preferably expressed as weight/volume; w/v) of proadrenomedullin (proADM) or a partial peptide or fragment thereof, in particular midregional proadrenomedullin (MR-proADM), in the sample taken from a patient.

Within the scope of this invention, the terms "IFI/IFD" are understood as described by the European Organization for Research and Treatment of Cancer/Invasive fungal infections (IFI) Cooperative Group; National Institute of Allergy and Infectious Diseases Mycoses Study Group (EORTC/MSG) Consensus Group in 2002 and 2008 (Ascioglu S, Rex J H, de Pauw B, Bennett J E, Bille J, Crokaert F, Denning D W, Donnelly J P, Edwards J E, Erjavec Z, Fiere D, Lortholary O, Maertens J, Meis J F, Patterson T F, Ritter J, Selleslag D, Shah P M, Stevens D A, Walsh T J; Invasive Fungal Infections Cooperative Group of the European Organization for Research and Treatment of Cancer; Mycoses Study Group of the National Institute of Allergy and Infectious Diseases; .Clin Infect Dis. 2002 Jan. 1; 34(1):7-14. Epub 2001 Nov. 26; De Pauw B, Walsh T J, Donnelly J P, Stevens D A, Edwards J E, Calandra T, Pappas P G, Maertens J, Lortholary O, Kauffman C A, Denning D W, Patterson T F, Maschmeyer G, Bille J, Dismukes W E, Herbrecht R, Hope W W, Kibbler C C, Kullberg B J, Marr K A, Munoz P, Odds F C, Perfect J R, Restrepo A, Ruhnke M, Segal B H, Sobel J D, Sorrell T C, Viscoli C, Wingard J R, Zaoutis T, Bennett J E; European Organization for Research and Treatment of Cancer/Invasive Fungal Infections Cooperative Group; National Institute of Allergy and Infectious Diseases Mycoses Study Group (EORTC/MSG) Consensus Group. Clin Infect Dis. 2008 Jun. 15; 46(12): 1813-21. doi: 10.1086/588660).

Within the scope of this invention, the terms "IFI/IFD" have also the meaning of a systemic, generalized, deep-seated, visceral and severe, life-threatening fungal infections, rather than a superficial, local, colonized, benign, self-limiting fungal disease or infection.

The terms "IFI/IFD" encompass the risk of an adverse event, like death and increased morbidity.

The term "patient" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

Preferred patients for diagnosis or risk stratification according to the invention are critically ill patients, in particular patients being immunomodulated due to medicaments or disease or due to means of inducing, enhancing, or suppressing an immune response including immunocompromised patients such as patients who underwent transplantation, patients with severe neutropenia or cancer patients. Hence, such mentioned patients are preferred for a risk-stratification according to the invention.

Preferred patients for diagnosis or a risk stratification according to the invention can be critically ill patients who are diagnosed with sepsis, severe sepsis or septic shock, or patients who have symptoms according to infectious diseases but no manifested sepsis, patients with local infections (e.g. respiratory tract, urinary tract, abdominal, skin, mucosa, genital, central nervous system), patients treated with mechanical ventilation, fluids, renal replacement therapy, patients receiving antifungal therapy, patients who underwent surgeries, in particular liver surgeries, patients with liver cirrhosis and patients who suffered a trauma (polytrauma).

The method of the invention can be used for patient management which refers to:
  the decision for admission to hospital or intensive care unit, the decision for relocation of the patient to a specialized hospital or a specialized hospital unit, the evaluation for an early discharge from the intensive care unit or hospital, the allocation of resources (e.g. physician and/or nursing staff, diagnostics, therapeutics).

For this reason, the invention relates to the diagnosis and/or risk stratification of IFI/IFD, in particular IFI/IFD caused by *Candida* spp. (e.g. *C. albicans, C. glabrata*), *Aspergillus* spp. (e.g. *Aspergillus fumigatus*), etc., which are the most common pathogens responsible for IFI/IFD, in particular IFI/IFD associated with sepsis or septic shock.

In a very preferred embodiment the invention relates to the diagnosis and/or risk stratification of IFI/IFD associated with sepsis and/or septic shock.

The term "IFI/IFD associated with sepsis and/or septic shock" particularly comprises the comorbidity of these indications, i.e. in addition to an existing underlying disease (index disease), namely IFI/IFD, an existing, diagnostically distinguishable disease profile, namely sepsis and/or septic shock, is determined, i.e. there is an associated disease profile. This approach allows to prevent the adverse outcome of a sepsis and/or septic shock due to the first IFI/IFD, if an anti-fungal agent (drug) is timely applied to a patient.

In another embodiment, the determination of proadrenomedullin (proADM) or a partial peptide or fragment thereof, in particular midregional proadrenomedullin (MR-proADM) can additionally take place with other markers, where the proadrenomedullin (proADM) or a partial peptide or fragment thereof, in particular midregional proadrenomedullin (MR-proADM) is/are contained in a marker combination (panel, cluster), specifically preferably those that already indicate IFI/IFD, in particular IFI/IFD associated with sepsis or septic shock.

For this reason, the invention relates to an embodiment of the method according to the invention where the determination is additionally carried out with at least one further marker or clinical score or clinical parameter selected from the group of C-reactive protein (CRP), cytokines, such as TNF-alpha, for example, interleukins, such as IL-10, IL-6, IL-22, IL17A and IL-17B, interleukin-1 ß, procalcitonin and fragments thereof, pro-atrial natriuretic peptide and fragments thereof (ANP, pro ANP), pro-arginine vasopressin and fragments thereof (AVP, pro-AVP, copeptin), angiotensin II, endothelin-1, glucans, interferon gamma (INF-gamma), beta-D-glucan, galactomannan, and adhesion molecules, such as VCAM or ICAM, sequential organ failure assessment score (SOFA), simplified acute physiology score (SAPSII score), the Acute Physiology and Chronic Health Evaluation II (APACHE II) score, the Pneumonia Severity Index (PSI) score, age, gender, family history, ethnicity, body weight, body mass index (BMI), systolic blood pressure, diastolic blood pressure, heart rate, temperature, from a patient to be examined.

In particular, detection of galactomannan in bodily fluid is used to diagnose invasive fungal (aspergillosis) infections in humans.

In another embodiment of the invention, the method according to the invention can be carried out by means of parallel or simultaneous determinations of the markers (e.g. multi-titer plates with 96 cavities and more), where the determinations are carried out on at least one patient sample.

Furthermore, the method according to the invention and its determinations can be carried out using an automated analysis device, particularly using a Kryptor (B.R.A.H.M.S GmbH, Hennigsdorf, Germany).

In another embodiment, the method according to the invention and its determinations can be carried out by means of a rapid test (e.g. a lateral flow test), for example using single-parameter or multi-parameter determinations.

Furthermore, the invention relates to the use of proadrenomedullin (proADM) or a partial peptide or fragment thereof, in particular midregional proadrenomedullin (MR-proADM), or contained in a marker combination (panel, cluster), for in vitro diagnosis and/or risk stratification of IFI/IFD, in particular IFI/IFD associated with sepsis or septic shock. The marker combination can contain another suitable marker, if necessary.

Determining (or measuring or detecting) the level of proadrenomedullin (proADM) or a partial peptide or fragment thereof, in particular midregional proadrenomedullin (MR-proADM), herein is performed using a detection method and/or a diagnostic assay as explained below.

Another object is making available a corresponding diagnostic assay, or the use of such an assay for carrying out the methods according to the invention.

As mentioned herein, an "assay" or "diagnostic assay" can be of any type applied in the field of diagnostics. Such an assay may be based on the binding of an analyte to be detected to one or more capture probes (capture molecules) with a certain affinity. Concerning the interaction between capture molecules and target molecules or molecules of interest, the affinity constant is preferably greater than $10^8$ $M^{-1}$.

Moreover, a marker can be determined by mass spectrometric based methods, such as methods determining the relative quantification or determining the absolute quantification of the protein or fragment thereof of interest.

Relative quantification "rSRM" may be achieved by:

1. Determining increased or decreased presence of the target protein by comparing the SRM (Selected reaction monitoring) signature peak area from a given target fragment peptide detected in the sample to the same SRM signature peak area of the target fragment peptide in at least a second, third, fourth or more biological samples.

2. Determining increased or decreased presence of target protein by comparing the SRM signature peak area from a given target peptide detected in the sample to SRM signature peak areas developed from fragment peptides from other proteins, in other samples derived from different and separate biological sources, where the SRM signature peak area comparison between the two samples for a peptide fragment are normalized for e.g. to amount of protein analyzed in each sample.

3. Determining increased or decreased presence of the target protein by comparing the SRM signature peak area for a given target peptide to the SRM signature peak areas from other fragment peptides derived from different proteins within the same biological sample in order to normalize changing levels of histones protein to levels of other proteins that do not change their levels of expression under various cellular conditions.

4. These assays can be applied to both unmodified fragment peptides and to modified fragment peptides of the target proteins, where the modifications include, but are not limited to phosphorylation and/or glycosylation, acetylation, methylation (mono, di, tri), citrullination, ubiquitinylation and where the relative levels of modified peptides are determined in the same manner as determining relative amounts of unmodified peptides.

Absolute quantification of a given peptide may be achieved by:

1. Comparing the SRM/MRM signature peak area for a given fragment peptide from the target proteins in an individual biological sample to the SRM/MRM signature peak area of an internal fragment peptide standard spiked into the protein lysate from the biological sample. The internal standard may be a labeled synthetic version of the fragment peptide from the target protein that is being interrogated or the labeled recombinant protein. This standard is spiked into a sample in known amounts before (mandatory for the recombinant protein) or after digestion, and the SRM/MRM signature peak area can be determined for both the internal fragment peptide standard and the native fragment peptide in the biological sample separately, followed by comparison of both peak areas. This can be applied to unmodified fragment peptides and modified fragment peptides, where the modifications include but are not limited to phosphorylation and/or glycosylation, acetylation, methylation (e.g. mono-, di-, or tri-methylation), citrullination, ubiquitinylation, and where the absolute levels of modified peptides can be determined in the same manner as determining absolute levels of unmodified peptides.

2. Peptides can also be quantified using external calibration curves. The normal curve approach uses a constant amount of a heavy peptide as an internal standard and a varying amount of light synthetic peptide spiked into the sample. A representative matrix similar to that of the test samples needs to be used to construct standard curves to account for a matrix effect. Besides, a reverse curve method circumvents the issue of endogenous analyte in the matrix, where a constant amount of light peptide is spiked on top of the endogenous analyte to create an internal standard and varying amount of heavy peptide are spiked to create a set of concentration standards. Test samples to be compared with either the normal or reverse curves are spiked with the same amount of standard peptide as the internal standard spiked into the matrix used to create the calibration curve.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of Lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex®-based bead arrays, protein microarray assays, and rapid test formats such as for instance immunochromatographic strip tests.

The assays can be homogenous or heterogeneous assays, competitive and non-competitive sandwich assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (The Immunoassay Handbook, Ed. David Wild, Elsevier L T D, Oxford; 3rd ed. (May 2005); Hultschig C et al., Curr Opin Chem Biol. 2006 February; 10(1):4-10)).

In a particularly preferred embodiment the assay comprises at least one or two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4', 7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562. Preferred chemiluminescent dyes are acridiniumesters.

Within the scope of this invention, such a diagnostic assay is particularly understood in the broadest sense to be a device for carrying out the method according to the invention.

Within the scope of this invention, a diagnostic assay for detecting and measuring a biomarker can be combined with an assay method to detect fungal pathogens or fungal molecules. For detecting fungal pathogens or fungal molecules, molecular diagnostic applications (e.g. PCR) or mass spectometry can be applied. Moreover, antibodies or detecting agents are preferred which specifically detect parts of the fungi, particularly parts of the e.g., active, growing fungi e.g. hypha or parts of the asexual reproduction bodies e.g. spores (so called ISCA Diagnostics).

The invention furthermore relates to a kit or the use of such a kit for in vitro diagnosis or risk stratification of IFI/IFD, in particular IFI/IFD associated with sepsis or septic shock, where a determination of proadrenomedullin (proADM) or a partial peptide or fragment thereof, in particular midregional proadrenomedullin (MR-proADM), or contained in a marker combination (panel, cluster), is carried out in a patient to be investigated, particularly taking into consideration the aforementioned embodiments. Such detection reagents comprise capture molecules like antibodies, etc.

The methods of the present invention may in part be computer-implemented or supported by a computer system. In the computer-system, the determined level of the marker(s) can be combined with other marker levels and/or parameters of the subject in order to calculate a score which is indicative for the diagnosis, prognosis, risk assessment and/or risk stratification. For example, the determined values may be entered (either manually by a health professional or automatically from the device(s) in which the respective marker level(s) has/have been determined) into the computer-system. The computer-system can be directly at the point-of-care (e.g. ICU or ED) or it can be at a remote location connected via a computer network (e.g. via the internet). Typically, the computer-system will store the values (e.g. marker level or parameters such as age, blood pressure, weight, sex, etc.) on a computer-readable medium and calculate the score based-on pre-defined and/or pre-stored reference levels or reference values. The resulting score will be displayed and/or printed for the user (typically a health professional such as a physician). Alternatively, or in addition, the associated prognosis, diagnosis, assessment or stratification will be displayed and/or printed for the user (typically a health professional such as a physician).

The following examples and figures serve for a more detailed explanation of the invention, but without restricting the invention to these examples and figures. The use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1

Study design. The observational clinical study was approved by the local ethics committee (Ethics Committee of the Medical Faculty of Heidelberg, Trial Code No. S-097/2013/German Clinical Trials Register: DRKS00005463) and was conducted in the surgical intensive care unit of Heidelberg University Hospital, Germany between November 2013 and January 2015. All study patients or their legal designees gave written informed consent. In total 50 patients suffering from septic shock according to the criteria of the Surviving Sepsis Campaign: International Guidelines for Management of Severe Sepsis and Septic Shock 2012 were enrolled in this study (Dellinger R P, Levy M M, Rhodes A et al. (2013) Surviving sepsis campaign: international guidelines for management of severe sepsis and septic shock: 2012. Crit Care Med 41:580-637. Treatment of patients with septic shock included early-goal directed therapy (Romani L (2004) Immunity to fungal infections. Nat Rev Immunol 4:1-23), elimination of the septic focus and broad-spectrum antibiosis Romani L (2004) Immunity to fungal infections. Nat Rev Immunol 4:1-23; Schroeder M, Simon M, Katchanov J et al. (2016) Does galactomannan testing increase diagnostic accuracy for IPA in the ICU? A prospective observational study. Crit Care 20:139; Zedek D C, Miller M B (2006) Use of galactomannan enzyme immunoassay for diagnosis of invasive aspergillosis in a tertiary-care center over a 12-month period. J Clin Microbiol 44:1601).

Blood samples were collected at sepsis onset (T0) and 1 day (T1), 2 days (T2), 7 days (T3) 14 days (T4), 21 days (T5) and 28 days (T6) afterwards. Relevant baseline data (demographic data, primary site of infection), clinical data (disease severity scores, such as Simplified Acute Physiology Score (SAPS II), Sequential Organ Failure Assessment Score (SOFA) and Acute Physiology Health Evaluation score (APACHE II), surgical procedures, antifungal therapy, outcome parameters) as well as routine infection parameters (e.g. leukocytes, C-reactive protein (CRP), procalcitonin (PCT), body temperature) were collected.

Immunoassays. Plasma concentrations of BG were measured using the Glucatell®-Kit (Pyroquant Diagnostik GmbH) according to the manufacturer's instructions. Plasma concentrations of MR-proADM were measured using a TRACE (Time Resolved Amplified Cryptate Emission) technology in combination with a new sandwich immunoassay (Kryptor Compact Plus Analyser, BRAHMS, Hennigsdorf, Germany). In all patients, concentrations of GM were measured using an enzyme-linked immunoassay (Platelia™ Aspergillus AG, Biorad, Munich) in plasma samples at all time points. Concentrations of GM in bronchoalveolar lavage fluid (BALF) were measured using the same technique, however only in selected cases of suspected invasive aspergillosis (IA). The following GM concentrations were used as cut-off values: Plasma>0.5, BALF>1.0.

Flowcytometry. Plasma concentrations of 11-2, IL-4, IL-6, IL-10, IL-17A, TNF-α and IFN-γ were measured on a FACSVerse flow cytometer (BD Biosciences, Heidelberg, Germany) using a multiplex assay (Human Th1/Th2/Th17 Cytokine Kit, BD Biosciences, Heidelberg, Germany) according to the manufacturer's instructions.

Clinical Microbiology.

Blood culture. Blood culture testing at Heidelberg University Hospital was routinely performed as described elsewhere (Gumbinger C, Hug A, Murle B et al. (2013) Early blood-based microbiological testing was ineffective in severe stroke patients. J Neurol Sci 325:46-50).

Whole blood samples were obtained via direct venipuncture (e.g., antecubital vein) applying sterile techniques and 10 mL blood was inoculated to both an aerobic and an anaerobic liquid culture medium (BACTEC PLUS, BD Biosciences, Heidelberg, Germany). Cultures were incubated for 5 days (BACTEC, BD Biosciences, Heidelberg, Germany) and positive cultures were analyzed according to approved inhouse hospital standard techniques, including identification by VITEK2 (Biomerieux, Nuertingen, Germany) or MALDI TOF (Bruker, Madison, Wis., USA) and automated antimicrobial susceptibility testing (VITEK 2).

Culture-based diagnostic procedures in tracheal secretion, wound swabs and drainage fluids. Briefly, tracheal aspirates and drainage fluids were streaked manually on Columbia (BD), chocolate (bM), MacConkey (bM), Schaedler and kanamycin-vancomycin (BD, Bi-plate) and chromogenic Candida agar (BD), while wound swabs were inoculated semi-automated by PREVI Isola™ instrument on the same agar types. All plates were incubated at 37° C. in 5% CO2 for 24 to 48 h, except the Schaedler-KV bi-plates, which were incubated at 37° C. in an anaerobic chamber (GasPak; Becton, Dickinson, Franklin Lakes, N.J.) for 48 h as described (Mischnik A, Mieth M, Busch C J et al. (2012) First evaluation of automated specimen inoculation for wound swab samples by use of the Previ Isola system compared to manual inoculation in a routine laboratory: finding a cost-effective and accurate approach. J Clin Microbiol 50:2732-2736). Bacterial and fungal colonies were identified by MALDI-ToF mass spectrometry and automated AST was performed on VITEK II instruments (bM).

Group definitions. *Candida* spp. in the respiratory tract or in fluids from drainages were classified as colonization. Positive results in blood cultures, intraoperative swabs and *Aspergillus* spp. in deep respiratory tract specimens with accompanying pulmonary infiltrates were classified as infection.

Anti-*Candida*-antibody titer. *Candida albicans* specific IgM, IgA and IgG antibodies in serum were detected and quantified using Serion ELISA Classic™ *Candida albicans* IgA/IgG/IgM (ESR 117A/G/M, Virion Serion, Wuerzburg, Germany) as described in the manufacturer's instructions using a Behring ELISA Processor (BEP III, Siemens Healthcare Diagnostics, Marburg, Germany), (Zou M, Tang L, Zhao S et al. (2012) Systematic review and meta-analysis of detecting galactomannan in bronchoalveolar lavage fluid for diagnosing invasive aspergillosis. PLoS One 7:e43347).

Statistical analyses. The resulting data were entered into an electronic database (Excel 2010; Microsoft Corp, Redmond, USA) and evaluated using the SPSS software (Version 21.0; SPSS, Inc., Chicago, USA). Categorical data were summarized using absolute and relative frequencies. Quantitative data were summarized using median with quartiles. The Kolmogorov-Smirnov test was applied to check for normal distribution. Due to non-normally distributed data, non-parametric methods for evaluation were used (Chi-square test for categorical data, Mann-Whitney U test for continuous data). Appropriate cut-off values for the detection of a fungal infection were calculated using ROC analyses. A p-value<0.05 was considered statistically significant. Concerning symbolism and higher orders of significance: p<0.05: *, p<0.01: , p<0.001: *.

Results

Patients' characteristics. In total, 50 patients with septic shock were included in the presented investigation. Patients' characteristics are presented in Table 1. The underlying septic focus was the abdomen (n=43; 86%), followed by the lung (n=6; 12%), as well as the urogenital tract (n=1; 2%). The overall 28-day as well as 90-day mortality was 22% (n=11) and 34% (n=17), respectively. The median length of ICU as well as hospital stay was 20 days, and 44 days, respectively.

TABLE 1

Patients' characteristics (n = 50)

| | | All patients (n = 50) | without fungal isolates (n = 17) | with fungal isolates (n = 33) | p for patients without fungal isolates vs. patients with fungal isolates |
|---|---|---|---|---|---|
| Gender male | | 38 (76) | 11 (64.7) | 27 (81.8) | 0.160 |
| Age | (years) | 66 (61-75) | 71 (64-80) | 66 (59-74) | 0.117 |
| BMI | (kg/m$^2$) | 27.2 (24.4-30.9) | 27.2 (25.7-34.9) | 26.9 (23.1-30.9) | 0.401 |
| Postoperatively peritonitis initial operation | | 31 | 9 (52.9) | 22 (66.7) | 0.206 |
| Kidney | | 2 (4) | 0 (0) | 2 (6.1) | 0.431 |
| Liver | | 11 (22) | 1 (2.1) | 10 (30.3) | 0.047* |
| Pancreas | | 2 (10) | 1 (5.9) | 1 (3.0) | 0.569 |
| GIT | | 38 ((76) | 14 (82.4) | 24 (72.7) | 0.350 |
| VAS | | 3 (6) | 2 (11.8) | 1 (3.0) | 0.264 |
| Others | | 12 (24) | 3 (17.6) | 9 (27.3) | 0.350 |
| ≥48 h after hospital admission | | 25 (50) | 7 (41.2) | 18 (54.5) | 0.276 |
| NYHA 0-I | | 41 (82) | 13 (76.4) | 28 (84.8) | 0.358 |
| Diabetes mellitus | | 17 (34) | 5 (29.4) | 12 (36.3) | 0.434 |
| Arterial hypertension | | 34 (68) | 12 (70.6) | 22 (66.7) | 0.520 |
| Coronary heart disease | | 8 (16) | 5 (29.4) | 3 (9.1) | 0.076 |
| Chronic obstructive lung disease | | 10 (20) | 5 (29.4) | 5 (15.2) | 0.204 |
| Renal insufficiency | | 7 (14) | 1 (5.9) | 6 (18.2) | 0.231 |
| Renal replacement therapy | | 15 (30) | 2 (11.8) | 13 (39.4) | 0.041* |
| Liver cirrhosis | | 13 (26) | 3 (17.6) | 10 (30.3) | 0.270 |
| Oncological disease | | 33 (66) | 11 (64.7) | 22 (66.7) | 0.566 |
| APACHE II* | | 30 (28-35) | 32 (28-36) | 30 (28-34) | 0.491 |
| SOFA* | | 11 (10-14) | 11 (10-14) | 11 (10-14) | 0.959 |
| SAPS* | | 65 (49-75) | 72 (48-75) | 65 (51-72) | 0.467 |
| *Candida* colonization | | 22 (44) | 0 (0) | 22 (66.7) | — |

TABLE 1-continued

Patients' characteristics (n = 50)

| | All patients (n = 50) | without fungal isolates (n = 17) | with fungal isolates (n = 33) | p for patients without fungal isolates vs. patients with fungal isolates |
|---|---|---|---|---|
| Candida infection | 10 (20) | 0 (0) | 10 (30.3) | — |
| Candidemia | 3 (6) | 0 (0) | 3 (9.1) | — |
| Aspergillus spp. | 1 (3) | 0 (0) | 1 (3.0) | — |
| Candida-Score | 4 (4-4) | 4 (4-4) | 4 (4-4) | 0.080 |
| Duration of mechanical ventilation (hours) | 145.5 (67.3-450) | 89 (46-145) | 181 (77-682) | 0.015* |
| ICU length of stay (days) | 19.5 (12-44) | 12 (3-17) | 24 (15-46) | 0.002** |
| Hospital length of stay (days) | 44 (23.3-68.5) | 24 (12-40) | 51 (39-78) | 0.007** |
| Tracheotomy | 14 (28) | 2 (11.8) | 12 (36.3) | 0.063 |
| Anastomosis leakage | 24 (48) | 7 (41.2) | 17 (51.5) | 0.347 |
| Fascia dehiscence | 12 (24) | 2 (11.8) | 10 (30.3) | 0.134 |
| 90-day mortality | 17 (34) | 8 (47.1) | 9 (27.3) | 0.175 |
| 28-day mortality | 11 (22) | 7 (41.2) | 4 (12.1) | 0.025* |

Data are presented as either number (with the corresponding percentage value) or median (with accompanying quartiles).

Data are presented as either number (with the corresponding percentage value) or median (with accompanying quartiles).

Fungal Pathogens and Infection Sites.

Culture-based microbiological diagnostics. As assessed by culture-based microbiological diagnostics, fungal pathogens were present in 33 patients (66.0%), whereas 17 patients (34.0%) revealed negative fungal cultures. Fungal isolates were found in one or multiple locations in 25 (75.8%), or 8 (24.2%) patients respectively and were located at the following sites: respiratory tract (n=17; 51.5%), abdominal site (n=21; 63.6%) and blood culture (n=3; 9.1%). Characteristics of patients with or without fungal pathogens are presented in Table 1. Patients with fungal pathogens underwent liver surgery more frequently prior to study inclusion and the need for renal replacement therapy was shown to be significantly increased. Concerning further markers for morbidity, fungal-positive patients revealed a significant prolonged duration of mechanical ventilation and the need for tracheostomy tended to be increased. Moreover, length of ICU as well as hospital stay was significantly prolonged in patients with fungal pathogens. Surprisingly, 28-day mortality was significantly increased in patients without fungal pathogens, whereas 90-day mortality was shown to be comparable.

Based on the group definitions as described in the methods section, colonization and infection was found in 22 (44.0%), and 11 (22.0%) patients, respectively. In colonized patients, 8 (16.0%) participants exclusively revealed Candida spp. in respiratory secretions (5× C. albicans, 1× C. albicans and glabrata, 2× C. albicans and C. spp.), whereas in 6 (12.0%) patients Candida spp. could only be cultured from drainage fluids (3× C. albicans, 2× C. glabrata, 1× C. albicans and C. glabrata). Contrariwise, 8 (16.0%) patients were colonized at both sides (4× C. albicans, 1× C. albicans and C. spp., 3× C. albicans and C. glabrata). In infected patients, fungemia was found in 3 (6.0%) patients (2× C. albicans, 1× C. glabrata) and positive abdominal wound swabs were found in 7 (14.0%) patients (4× C. albicans, 1× C. glabrata, 1× C. krusei, 1× C. albicans and C. glabrata). Moreover, in one (2.0%) patient Aspergillus fumigatus was isolated in respiratory tract secretions. Concerning risk factors, liver surgery prior to study inclusion as well as liver cirrhosis could be observed more frequently in patients with a fungal infection. Moreover, the duration of ICU stays as well as mechanical ventilation was significantly prolonged and the need for tracheotomy was significantly increased in patients suffering from a fungal infection. Although morbidity was shown to be increased, mortality at 28 and 90 days did not differ significantly between infected and uninfected patients.

Antifungal therapy. In total, 21 of 50 (42.0%) patients received an antifungal therapy during study participation. Of 17 patients without any fungal isolates, 2 (11.8%) patients received an empiric antifungal therapy. Of the remaining 33 patients with fungal isolates, 19 (57.6%) patients received an antifungal therapy, which was initiated in terms a specific therapy in 15 (78.9%) patients. Vice versa, treatment was initiated in terms of an empiric therapy in the remaining 4 (21.1%) cases, which was stopped later on in all of these patients. In 7 (33.3%) patients, the initial antifungal therapy was changed in the course of the disease.

(1,3)-ß-D-glucan (BG). Plasma concentrations of BG were comparable between the three subgroups throughout the entire study period and therefore failed to be of diagnostic value for the prediction of a fungal infection (data not shown). Even in patients suffering from candidemia, plasma concentrations of BG were not increased reliably.

Galactomannan (GM). Plasma concentrations of GM remained below the cut-off value of <0.5 in 46 of 50 patients (92.0%). Contrariwise, 4 patients (8.0%) presented with sporadically increased plasma concentrations of GM above the cut-off value without any other (clinical, radiological, cultural) signs or risk factors for an IA (data not shown). In these cases, increased plasma concentrations of GM were most probably attributable to the underlying antibiotic therapy (e.g. piperacillin-tazobactam), which is well known to be associated with increased GM concentrations (Boonsarngsuk, V.; Niyompattama, A.; Teosirimongkol, C.; Sriwanichrak, K. False—positive serum and bronchoalveolar lavage aspergillus galactomannan assays caused by different antibiotics. Scand. J. Infect. Dis. 2010, 42, 461-468; Metan, G. The interaction between piperacillin-tazobactam and aspergillus galactomannan antigenemia assay: Is the story over? Infection 2013, 41, 293-294).

One patient presented with the diagnosis of an IA as assessed by cultural detection of Aspergillus fumigatus in BALF, which was confirmed by high-resolution computed tomography. Moreover, GM concentrations in BALF were increased above the cut-off value, whereas plasma concentrations of GM remained below the cut-off value at all time points. Apart from septic shock as well as preexisting adipositas per magna and insulin-depending diabetes mellitus, the patient did not suffer from classical predisposing risk factors for IA (e.g. neutropenia, hemato-oncological diseases treated with cytotoxic agents, intake of corticosteroids, innate or acquired immunodeficiency). The patient was treated with liposomal amphotericin B for 6 weeks, which led to a decrease of GM in BALF below the cut-off value. Moreover, culture of BALF remained negative for *Aspergillus fumigatus* after the end the treatment period.

Anti-*Candida* antibody titer. In the subgroup of patients without any fungal findings (n=17), 4 patients (23.5%) presented with a "false" positive anti-*Candida* antibody titer (>1:320), whereas colonized patients (n=22) were shown to have positive test results in 81.8% (n=18). Patients suffering from a fungal infection (n=11) also revealed positive test results in 81.8% (n=9), but unfortunately two patients presenting with candidemia (at sepsis onset) failed to show a positive anti-*Candida* antibody titer.

With regard to fungal immunity, special caution should be given to the plasma levels of INF-β, IL-4, -6, -10, -17 as well as MR-proADM. Plasma levels of the pro-inflammatory cytokine INF-γ were shown to be markedly, respectively significantly elevated in patients suffering from a fungal infection in comparison to both control groups, starting from seven days after sepsis onset (T3). This increase in INF-γ was paralleled by a significant release of the immunosuppressive cytokines IL-10 and -4 in infected patients. Plasma levels of IL-6 were shown to be significantly elevated in patients suffering from a fungal infection in comparison to septic patients with a fungal colonization or without any fungal findings at different time points especially in the early course of the disease (e.g. at T0, T1). In parallel, IL-17A was also shown to be significantly increased in septic patients suffering from a fungal infection in comparison to septic patients with a fungal colonization or without any fungal findings within the first 7 days after sepsis onset (FIG. 2A).

Figure 2B:
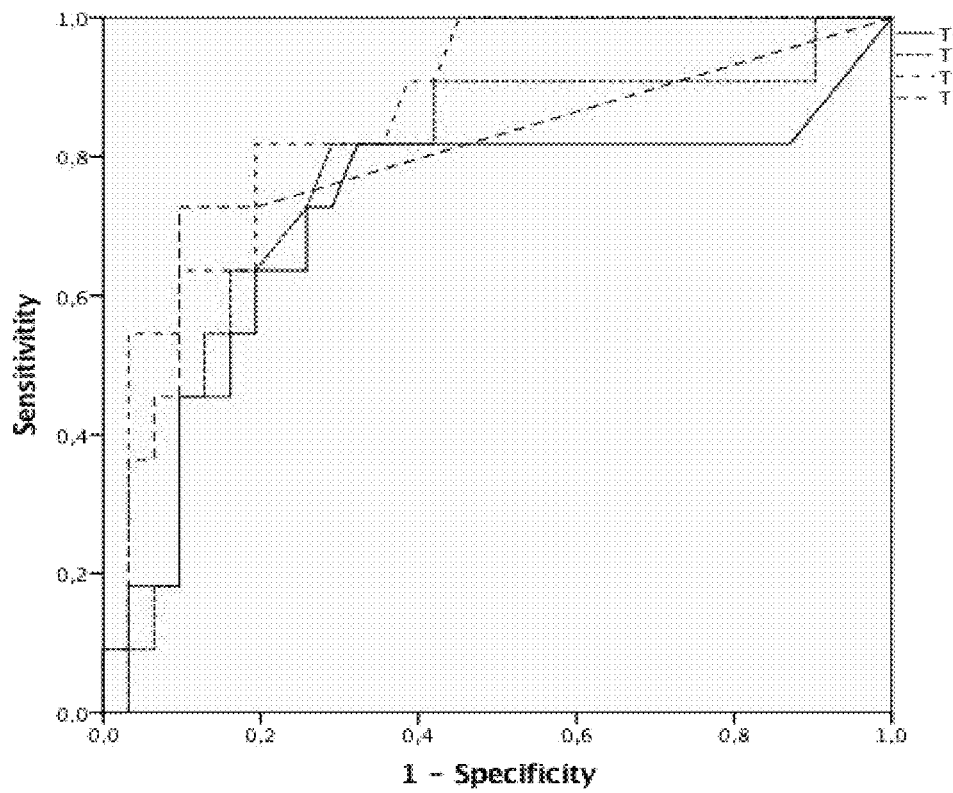

Therefore, IL-17A was found to be a suitable tool for early identification of patients with a fungal infection as assessed by ROC-analysis (ROC-AUC for patients with a fungal infection vs. non-infected patients (=patients without any fungal isolates+colonized patients) e.g. at t0: 0.714; Cut-Off 14.165 pg/ml→Sens. 0.818; 1-Spec. 0.323, t1: 0.776; Cut-Off: 14.22 pg/ml→Sens. 0.818; 1-Spec. 0.29, t2: 0.865 Cut-Off 15.00 pg/ml→Sens. 0.818; 1-Spec. 0.194, etc.) (FIG. 2B).

Figure 3A:
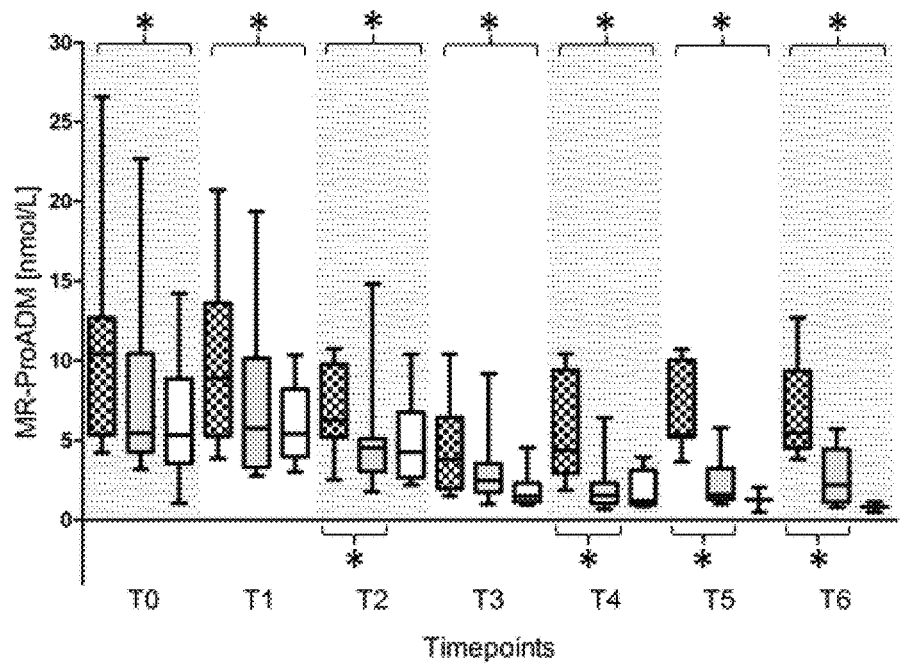
FIGS. 3A and 3B show plasma concentrations of midregional proAdrenomedullin (MR-proADM) in patients with septic shock.
Figure 3B:
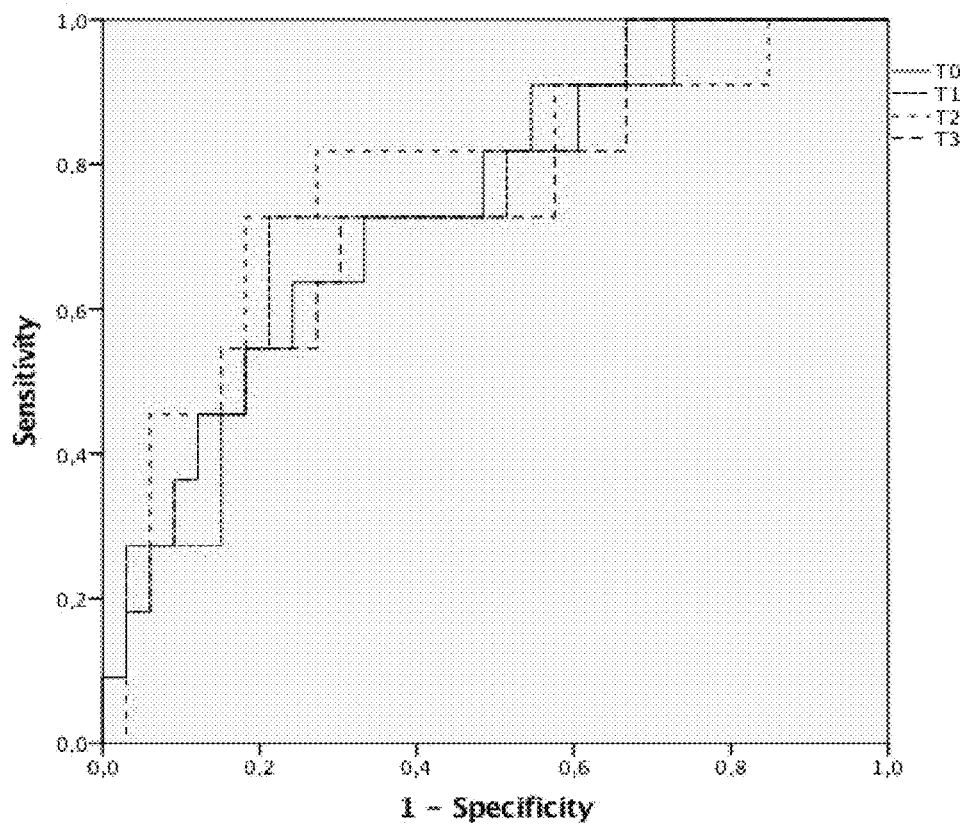

The same holds true for plasma levels of MR-proADM, which were shown to be significantly increased in infected patients in comparison to colonized patients as well as patients without any fungal findings (FIG. 3A). Accordingly, MR-proADM was shown to be a suitable tool for the identification of patients with a fungal infection as assessed by a receiver operating characteristic (ROC)-analyses (ROC-area under the curve (AUC) for patients with a fungal infection vs. non-infected patients (=see above) e.g. at t0: 0.738; Cut-Off: 6.99 nmol/l→Sens. 0.727; 1-Spec. 0.333, t1: 0.755; Cut-Off: 8.53 nmol/l→Sens. 0.727; 1-Spec. 0.212, t2: 0.774; Cut-Off 5.10 nmol/l→Sens. 0.818; 1-Spec. 0.273, etc.) (FIG. 3B).

TABLE 2

Plasma levels of different infection and inflammation markers.

| | without fungal isolates | fungal colonization | fungal infection |
|---|---|---|---|
| | T0 | | |
| leukocytes 1/nl | 8.37 (7.12-14.47) | 13.43 (3.17-25.75) | 13.12 (10.78-19.52) |
| + | | 0.532 | |
| ++ | | 0.175 | |
| +++ | | 0.778 | |
| CRP (mg/l) | 190.9 (123.7-268.5) | 201.3 (151.7-293.4) | 167.1 (157.5-236.0) |
| + | | 0.180 | |
| ++ | | 0.942 | |
| +++ | | 0.693 | |
| PCT (ng/ml) | 3.06 (1.21-34.30) | 7.71 (4.04-14.03) | 17.60 (6.88-31.97) |
| + | | 0.754 | |
| ++ | | 0.492 | |
| +++ | | 0.297 | |
| TNF-α (pg/ml) | 0.04 (0.00-1.42) | 0.00 (0.00-0.89) | 0.76 (0.00-1.47) |
| + | | 0.726 | |
| ++ | | 0.487 | |
| +++ | | 0.357 | |
| IL-2 (pg/ml) | 0.06 (0.00-0.68) | 0.00 (0.00-0.88) | 0.00 (0.00-2.69) |
| + | | 0.878 | |
| ++ | | 0.789 | |
| +++ | | 0.638 | |
| IL-4 (pg/ml) | 0.00 (0.00-0.24) | 0.08 (0.00-0.96) | 0.00 (0.00-1.30) |
| + | | 0.362 | |
| ++ | | 0.517 | |
| +++ | | 0.985 | |
| IL-6 (pg/ml) | 12815.5 (1104.4-22524.8) | 1944.2 (596.4-5603.9) | 8414.9 (3352.8-13318.1) |
| + | | 0.279 | |
| ++ | | 0.817 | |
| +++ | | 0.006** | |
| IL-10 (pg/ml) | 14.63 (4.87-53.78) | 15.08 (6.19-24.90) | 18.74 (8.12-86.42) |
| + | | 0.922 | |
| ++ | | 0.746 | |
| +++ | | 0.866 | |
| IFN-γ (pg/ml) | 0.00 (0.00-0.33) | 0.00 (0.0-0.76) | 0.00 (0.00-2.20) |
| + | | 0.747 | |
| ++ | | 0.430 | |
| +++ | | 0.638 | |
| | T1 | | |
| leukocytes 1/nl | 19.76 (7.93-24.33) | 19.76 (13.14-28.69) | 17.27 (14.81-25.31) |
| + | | 0.082 | |
| ++ | | 0.687 | |
| +++ | | 0.815 | |
| CRP (mg/l) | 261.0 (204.5-307.2) | 275.7 (218.0-335.3) | 247.5 (184.7-282.3) |
| + | | 0.000*** | |
| ++ | | 0.647 | |
| +++ | | 0.531 | |
| PCT (ng/ml) | 6.29 (2.88-28.26) | 4.09 (1.86-23.97) | 19.09 (7.91-38.65) |
| + | | 0.055 | |
| ++ | | 0.524 | |
| +++ | | 0.254 | |
| TNF-α (pg/ml) | 0.00 (0.00-0.56) | 0.16 (0.00-1.68) | 0.04 (0.00-1.85) |

TABLE 2-continued

Plasma levels of different infection and inflammation markers.

| | without fungal isolates | fungal colonization | fungal infection |
|---|---|---|---|
| + | | 0.2010 | |
| ++ | | 0.403 | |
| +++ | | 0.755 | |
| IL-2 (pg/ml) | 0.16 (0.00-0.45) | 0.20 (0.00-2.05) | 0.47 (0.00-1.84) |
| + | | 0.516 | |
| ++ | | 0.789 | |
| +++ | | 0.907 | |
| IL-4 (pg/ml) | 0.00 (0.00-0.21) | 0.44 (0.00-2.53) | 0.44 (0.06-0.91) |
| + | | 0.118 | |
| ++ | | 0.066 | |
| +++ | | 0.969 | |
| IL-6 (pg/ml) | 460.9 (140.8-1005.00) | 209.0 (104.3-468.2) | 359.3 (202.7-1016.8) |
| + | | 0.278 | |
| ++ | | 0.936 | |
| +++ | | 0.048* | |
| IL-10 (pg/ml) | 4.47 (1.45-5.87) | 5.31 (2.05-10.33) | 6.61 (4.22-11.03) |
| + | | 0.516 | |
| ++ | | 0.095 | |
| +++ | | 0.254 | |
| IFN-γ (pg/ml) | 0.03 (0.00-0.20) | 0.14 (0.00-1.82) | 1.37 (0.07-2.94) |
| + | | 0.309 | |
| ++ | | 0.051 | |
| +++ | | 0.434 | |
| T2 | | | |
| leukocytes 1/nl | 16.87 (8.03-22.03) | 21.42 (17.23-28.07) | 15.08 (11.16-26.12) |
| + | | 0.000*** | |
| ++ | | 0.910 | |
| +++ | | 0.168 | |
| CRP (mg/l) | 294.5 (214.0-337.5) | 252.8 (170.3-315.8) | 224.0 (172.9-303.1) |
| + | | 0.002** | |
| ++ | | 0.392 | |
| +++ | | 0.938 | |
| PCT (ng/ml) | 3.49 (1.88-36.69) | 3.88 (3.32-4.60) | 21.29 (16.04-26.53) |
| + | | 0.200 | |
| ++ | | 1.000 | |
| +++ | | 0.200 | |
| TNF-α (pg/ml) | 0.04 (0.00-1.51) | 0.52 (0.00-1.85) | 1.06 (0.09-1.95) |
| + | | 0.596 | |
| ++ | | 0.277 | |
| +++ | | 0.553 | |
| IL-2 (pg/ml) | 0.06 (0.00-0.13) | 0.00 (0.00-1.55) | 0.45 (0.14-1.69) |
| + | | 0.705 | |
| ++ | | 0.134 | |
| +++ | | 0.525 | |
| IL-4 (pg/ml) | 0.00 (0.00-0.54) | 0.00 (0.00-1.62) | 0.37 (0.00-0.82) |
| + | | 0.762 | |
| ++ | | 0.649 | |
| +++ | | 0.899 | |
| IL-6 (pg/ml) | 92.3 (57.9-246.0) | 57.3 (24.7-149.1) | 80.6 (41.9-157.9) |
| + | | 0.323 | |
| ++ | | 0.865 | |
| +++ | | 0.180 | |
| IL-10 (pg/ml) | 2.39 (1.13-4.86) | 3.80 (0.93-6.73) | 4.10 (2.25-6.17) |
| + | | 0.762 | |
| ++ | | 0.392 | |
| +++ | | 0.420 | |
| IFN-γ (pg/ml) | 0.00 (0.00-0.21) | 0.00 (0.00-2.04) | 0.81 (0.00-4.31) |
| + | | 0.791 | |
| ++ | | 0.134 | |
| +++ | | 0.328 | |
| T3 | | | |
| leukocytes 1/nl | 14.66 (11.07-17.03) | 15.98 (13.23-23.16) | 16.87 (11.31-24.82) |
| + | | 0.177 | |
| ++ | | .0314 | |
| +++ | | 0.917 | |
| CRP (mg/l) | 141.0 (98.8-189.4) | 138.9 (116.0-176.1) | 132.6 (118.1-156.1) |
| + | | 0.096 | |
| ++ | | 0.809 | |
| +++ | | 1.000 | |
| PCT (ng/ml) | 0.32 (0.15-0.60) | 0.57 (0.36-1.00) | 5.38 (4.30-5.55) |
| + | | 0.222 | |
| ++ | | 0.029* | |
| +++ | | 0.008** | |
| TNF-α (pg/ml) | 0.00 (0.00-0.00) | 0.00 (0.00-0.00) | 0.18 (0.00-0.33) |
| + | | 0.897 | |
| ++ | | 0.013* | |
| +++ | | 0.008** | |
| IL-2 (pg/ml) | 0.04 (0.00-0.08) | 0.00 (0.00-0.04) | 0.37 (0.00-0.75) |
| + | | 0.187 | |
| ++ | | 0.169 | |
| +++ | | 0.046* | |
| IL-4 (pg/ml) | 0.00 (0.00-0.00) | 0.00 (0.00-0.00) | 0.18 (0.07-0.62) |
| + | | 0.754 | |
| ++ | | 0.001*** | |
| +++ | | 0.001*** | |
| IL-6 (pg/ml) | 20.0 (3.3-132.4) | 30.6 (21.1-97.1) | 142.9 (93.8-261.1) |
| + | | 0.494 | |
| ++ | | 0.051 | |
| +++ | | 0.031* | |
| IL-10 (pg/ml) | 0.59 (0.18-1.17) | 0.57 (0.39-1.30) | 1.54 (0.63-2.89) |
| + | | 0.449 | |
| ++ | | 0.032* | |
| +++ | | 0.061 | |
| IFN-γ (pg/ml) | 0.00 (0.00-0.32) | 0.00 (0.00-0.08) | 1.09 (0.08-1.49) |
| + | | 0.754 | |
| ++ | | 0.027* | |
| +++ | | 0.006** | |
| T4 | | | |
| leukocytes 1/nl | 9.35 (7.88-10.79) | 11.55 (9.50-17.93) | 15.62 (10.80-19.31) |
| + | | 0.421 | |
| ++ | | 0.050* | |
| +++ | | 0.452 | |
| CRP (mg/l) | 125.1 (84.2-170.8) | 146.7 (73.0-156.3) | 130.6 (77.8-168.6) |
| + | | 0.301 | |
| ++ | | 1.000 | |
| +++ | | 0.825 | |
| PCT (ng/ml) | 0.00 (0.00-0.00) | 1.21 (0.60-1.81) | 1.92 (1.70-2.15) |
| + | | 1.000 | |

TABLE 2-continued

Plasma levels of different infection and inflammation markers.

| | without fungal isolates | fungal colonization | fungal infection |
|---|---|---|---|
| ++ | | 1.000 | |
| +++ | | 1.000 | |
| TNF-α (pg/ml) | 0.00 (0.00-0.00) | 0.00 (0.00-0.00) | 0.00 (0.00-0.39) |
| + | | 0.637 | |
| ++ | | 0.113 | |
| +++ | | 0.136 | |
| IL-2 (pg/ml) | 0.00 (0.00-0.13) | 0.00 (0.00-0.00) | 0.18 (0.10-0.88) |
| + | | 0.357 | |
| ++ | | 0.063 | |
| +++ | | 0.010** | |
| IL-4 (pg/ml) | 0.00 (0.00-0.00) | 0.00 (0.00-0.01) | 0.13 (0.0-0.90) |
| + | | 0.522 | |
| ++ | | 0.024* | |
| +++ | | 0.043* | |
| IL-6 (pg/ml) | 11.7 (3.0-28.9) | 18.3 (11.7-185.4) | 138.2 (74.7-268.6) |
| + | | 0.169 | |
| ++ | | 0.006** | |
| +++ | | 0.152 | |
| IL-10 (pg/ml) | 0.16 (0.11-0.51) | 0.25 (0.11-0.60) | 1.19 (0.96-2.12) |
| + | | .0637 | |
| ++ | | 0.001*** | |
| +++ | | 0.002** | |
| IFN-γ (pg/ml) | 0.00 (0.00-0.00) | 0.00 (0.00-0.00) | 0.26 (0.17-2.51) |
| + | | 0.718 | |
| ++ | | 0.006* | |
| +++ | | 0.004* | |
| T5 | | | |
| leukocytes 1/nl | 8.01 (6.58-10.83) | 11.71 (9.90-19.15) | 23.09 (11.43-29.46) |
| + | | 0.000*** | |
| ++ | | 0.117 | |
| +++ | | 0.227 | |
| CRP (mg/l) | 65.6 (58.3-88.0) | 113.0 (91.2-144.8) | 134.0 (111.1-151.5) |
| + | | 0.003** | |
| ++ | | 0.492 | |
| +++ | | 0.563 | |
| PCT (ng/ml) | 0.00 (0.00-0.00) | 0.00 (0.00-0.00) | 0.82 (0.62-1.02) |
| + | | 0.111 | |
| ++ | | 1.000 | |
| +++ | | 1.000 | |
| TNF-α (pg/ml) | 0.00 (0.00-0.00) | 0.00 (0.00-0.00) | 0.58 (0.00-1.57) |
| + | | 0.900 | |
| ++ | | 0.183 | |
| +++ | | 0.067 | |
| IL-2 (pg/ml) | 0.00 (0.00-0.01) | 0.00 (0.00-0.04) | 0.88 (0.26-1.64) |
| + | | 0.704 | |
| ++ | | 0.067 | |
| +++ | | 0.003** | |
| IL-4 (pg/ml) | 0.00 (0.00-0.00) | 0.00 (0.00-0.00) | 0.31 (0.05-1.05) |
| + | | 0.900 | |
| ++ | | 0.117 | |
| +++ | | 0.014* | |
| IL-6 (pg/ml) | 4.7 (3.9-6.5) | 21.9 (12.0-46.1) | 61.2 (11.9-144.3) |
| + | | 0.014* | |
| ++ | | 0.033* | |
| +++ | | 0.643 | |
| IL-10 (pg/ml) | 0.03 (0.01-0.06) | 0.35 (0.18-0.42) | 1.45 (1.26-2.88) |
| + | | 0.082 | |
| ++ | | 0.067 | |
| +++ | | 0.030* | |
| IFN-γ (pg/ml) | 0.00 (0.00-0.00) | 0.00 (0.00-0.08) | 1.86 (0.00-3.64) |
| + | | 0.364 | |
| ++ | | 0.183 | |
| +++ | | 0.157 | |
| T6 | | | |
| leukocytes 1/nl | 8.84 (7.97-9.70) | 12.97 (10.52-15.44) | 20.49 (14.87-22.26) |
| + | | 0.000*** | |
| ++ | | 0.333 | |
| +++ | | 0.456 | |
| CRP (mg/l) | 69.7 (69.7-69.8) | 64.3 (39.2-97.1) | 102.8 (64.2-147.9) |
| + | | 0.040* | |
| ++ | | 0.524 | |
| +++ | | 0.165 | |
| PCT (ng/ml) | 0.00 (0.00-0.00) | 0.00 (0.00-0.00) | 2.53 (1.92-3.14) |
| + | | 0.133 | |
| ++ | | 1.000 | |
| +++ | | 1.000 | |
| TNF-α (pg/ml) | 0.00 (0.00-0.00) | 0.00 (0.00-0.00) | 1.19 (0.00-3.64) |
| + | | 1.00 | |
| ++ | | 0.333 | |
| +++ | | 0.094 | |
| IL-2 (pg/ml) | 0.06 (0.04-0.08) | 0.14 (0.06-0.20) | 1.54 (0.12-2.43) |
| + | | 0.533 | |
| ++ | | 0.333 | |
| +++ | | 0.121 | |
| IL-4 (pg/ml) | 0.00 (0.00-0.00) | 0.01 (0.00-0.05) | 0.79 (0.22-1.55) |
| + | | 0.400 | |
| ++ | | 0.111 | |
| +++ | | 0.040* | |
| IL-6 (pg/ml) | 3.2 (2.9-3.5) | 13.9 (6.6-28.2) | 54.1 (41.7-161.4) |
| + | | 0.089 | |
| ++ | | 0.056 | |
| +++ | | 0.004** | |
| IL-10 (pg/ml) | 0.02 (0.01-0.03) | 0.31 (0.13-0.41) | 2.53 (1.27-3.02) |
| + | | 0.267 | |
| ++ | | 0.056 | |
| +++ | | 0.006** | |
| IFN-γ (pg/ml) | 0.00 (0.00-0.00) | 0.00 (0.00-0.12) | 3.50 (0.17-4.45) |
| + | | 0.533 | |
| ++ | | 0.111 | |
| +++ | | 0.029* | |

Data are presented as median with accompanying quartiles (Q1, Q3).
Legends:
+ = patients without fungal isolates vs. colonized patients,
++ = patients without fungal isolates vs. infected patients,
+++ = colonized vs. infected patients.
Plasma samples were collected at the onset of septic shock (T0), and 1 day (T1), 2 days (T2), 7 days (T3), 14 days (T4), 21 days (T5) and 28 days (T6) afterwards.
$p < 0.05$: *,
$p < 0.01$: **,
$p < 0.001$: ***.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. Method for diagnosing and treating an invasive fungal infections (IFI) and/or invasive fungal diseases (IFD) in a patient, comprising:
providing at least one sample taken from the patient
measuring the presence of proadrenomedullin (proADM) (SEQ ID No: 6) or a partial peptide or fragment thereof, in said sample from the patient,
wherein a level of proADM (SEQ ID NO:6) or a partial peptide or fragment thereof, is above a predetermined threshold value and
treating the patient for invasive fungal infections (IFI) and/or invasive fungal diseases (IFD) by administering at least one anti-fungal agent to the patient.

2. The method of claim 1 wherein the invasive fungal infections (WI) and/or invasive fungal diseases (IFD) are associated with sepsis and/or septic shock.

3. The method of claim 1, wherein said fragments are at least one of the group of 22-41 amino acids of pre-pro-ADM (PAMP) (SEQ ID No: 2), MR-proADM (midregional proadrenomedullin) (SEQ ID No: 3), ADM (Adrenomedullin) (SEQ ID No: 4), CT-pro-ADM (Adrenotensin) (SEQ ID No: 5).

4. The method of claim 1, wherein said invasive fungal infections (IFI) and/or invasive fungal diseases (IFD) is/are caused by *Candida* spp., *C. albicans, C. glabrata, Aspergillus* spp. *Aspergillus fumigatus.*

5. The method of claim 1, additionally comprising
measuring at least one further marker and/or clinical score and/or clinical parameter selected from the group consisting of C-reactive protein (CRP), cytokines, procalcitonin and fragments thereof, pro-atrial natriuretic peptide and fragments thereof (ANP, pro ANP), pro-arginin vasopressin and fragments thereof(AVP, pro-AVP, copeptin), angiotensin II, endothelin-1, glucans, interferon gamma (INF-gamma), beta-D-glucan, galactomannan, and adhesion molecules, sequential organ failure assessment score (SOFA), simplified acute physiology score (SAPSII score), the Acute Physiology and Chronic Health Evaluation II (APACHE II) score, the Pneumonia Severity Index (PSI) score, age, gender, family history, ethnicity, body weight, body mass index (BMI), systolic blood pressure, diastolic blood pressure, heart rate, and temperature from a patient to be examined.

6. The method of claim 5,
wherein parallel or simultaneous measurements of two or more of the markers are carried out.

7. The method of claim 1,
wherein the measurements are carried out on at least two patient samples.

8. The method of claim 1,
wherein the measurement is made with an automated analysis device or diagnostic assay.

9. The method of claim 1,
wherein the measurement is made with a rapid test with single-parameter or multi-parameter determinations.

10. The method of claim 1,
wherein the at least one anti-fungal agent is selected from the group consisting of polyene anti-fungal drugs, echinocandins, azole anti-fungal drugs, allylamine and morpholine anti-fungal drugs, and antimetabolite anti-fungal drugs.

11. The method of claim 10,
wherein the patients are selected from the group of patients consisting of being critically ill, wherein the patient is immunomodulated due to medicaments or disease or due to means of inducing, enhancing, or suppressing an immune response including immunocompromised patients, severe neutropenia, and cancer patients.

12. The method of claim 1,
wherein the predetermined threshold value is defined as follows:
directly after occurrence of symptoms of infectious diseases (t=0), the predetermined threshold value is equal or higher than 6.99 nmol/L,
one day after occurrence of symptom of infectious diseases (t=1d) the predetermined threshold value is equal or higher than 8.53 nmol/L,
two days after occurrence of symptom of infectious diseases (t=2d) the predetermined threshold value is equal or higher than 5.10 nmol/L.

13. The method of claim 1,
wherein the predetermined threshold value is 5 nmol/L.

14. The method of claim 1,
wherein the measurement is taken directly after occurrence of the symptoms (t=0) and the predetermined threshold value is 2 nmol/L.

15. The method of claim 1 wherein the partial peptide or fragment thereof is midregional proadrenomedullin (MR-proADM) (SEQ ID No: 3).

16. The method of claim 1,
wherein the anti-fungal agent is suited for treating IFI and/or IFD caused by *Candida* spp., *C. albicans, C. glabrata, Aspergillus* spp. or *Aspergillus fumigatus.*

17. The method of claim 1,
wherein the anti-fungal agent is selected from the group consisting of polyene anti-fungal drugs, echinocandins, azole anti-fungal drugs, allylamine and morpholine anti-fungal drugs, and antimetabolite antifungal drugs.

18. The method of claim 1,
wherein the anti-fungal agent is administered by an intravenous administration.

* * * * *

SEQUENCE LISTING

```
<160> NUMBER OF SEQ ID NOS: 6

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 20
<212> TYPE: PRT
<213> ORGANISM: Homo sapiens

<400> SEQUENCE: 2

Ala Arg Leu Asp Val Ala Ser Glu Phe Arg Lys Lys Trp Asn Lys Trp
1               5                   10                  15

Ala Leu Ser Arg
            20

<210> SEQ ID NO 3
<211> LENGTH: 48
<212> TYPE: PRT
<213> ORGANISM: Homo sapiens

<400> SEQUENCE: 3

Glu Leu Arg Met Ser Ser Ser Tyr Pro Thr Gly Leu Ala Asp Val Lys
1               5                   10                  15
```

Ala Gly Pro Ala Gln Thr Leu Ile Arg Pro Gln Asp Met Lys Gly Ala
            20                  25                  30

Ser Arg Ser Pro Glu Asp Ser Ser Pro Asp Ala Ala Arg Ile Arg Val
            35                  40                  45

<210> SEQ ID NO 4
<211> LENGTH: 52
<212> TYPE: PRT
<213> ORGANISM: Homo sapiens

<400> SEQUENCE: 4

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
            35                  40                  45

Pro Gln Gly Tyr
    50

<210> SEQ ID NO 5
<211> LENGTH: 33
<212> TYPE: PRT
<213> ORGANISM: Homo sapiens

<400> SEQUENCE: 5

Ser Leu Pro Glu Ala Gly Pro Gly Arg Thr Leu Val Ser Ser Lys Pro
1               5                   10                  15

Gln Ala His Gly Ala Pro Ala Pro Pro Ser Gly Ser Ala Pro His Phe
            20                  25                  30

Leu

<210> SEQ ID NO 6
<211> LENGTH: 164
<212> TYPE: PRT
<213> ORGANISM: Homo sapiens

<400> SEQUENCE: 6

Ala Arg Leu Asp Val Ala Ser Glu Phe Arg Lys Lys Trp Asn Lys Trp
1               5                   10                  15

Ala Leu Ser Arg Gly Lys Arg Glu Leu Arg Met Ser Ser Ser Tyr Pro
            20                  25                  30

Thr Gly Leu Ala Asp Val Lys Ala Gly Pro Ala Gln Thr Leu Ile Arg
            35                  40                  45

Pro Gln Asp Met Lys Gly Ala Ser Arg Ser Pro Glu Asp Ser Ser Pro
    50                  55                  60

Asp Ala Ala Arg Ile Arg Val Lys Arg Tyr Arg Gln Ser Met Asn Asn
65                  70                  75                  80

Phe Gln Gly Leu Arg Ser Phe Gly Cys Arg Phe Gly Thr Cys Thr Val
                85                  90                  95

Gln Lys Leu Ala His Gln Ile Tyr Gln Phe Thr Asp Lys Asp Lys Asp
            100                 105                 110

Asn Val Ala Pro Arg Ser Lys Ile Ser Pro Gln Gly Tyr Gly Arg Arg
            115                 120                 125

Arg Arg Arg Ser Leu Pro Glu Ala Gly Pro Gly Arg Thr Leu Val Ser
        130                 135                 140

```
Ser Lys Pro Gln Ala His Gly Ala Pro Ala Pro Pro Ser Gly Ser Ala
145                 150                 155                 160

Pro His Phe Leu
```